United States Patent
Cho et al.

(10) Patent No.: US 8,628,963 B2
(45) Date of Patent: Jan. 14, 2014

(54) MEDIUM COMPOSITION COMPRISING NEUROPEPTIDE Y FOR THE GENERATION, MAINTENANCE, PROLONGED UNDIFFERENTIATED GROWTH OF PLURIPOTENT STEM CELLS AND METHOD OF CULTURING PLURIPOTENT STEM CELL USING THE SAME

(75) Inventors: Yee Sook Cho, Daejeon (KR); Mi-Young Son, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/378,912

(22) PCT Filed: Jun. 16, 2010

(86) PCT No.: PCT/KR2010/003891
§ 371 (c)(1),
(2), (4) Date: Mar. 2, 2012

(87) PCT Pub. No.: WO2010/147395
PCT Pub. Date: Dec. 23, 2010

(65) Prior Publication Data
US 2012/0171766 A1    Jul. 5, 2012

(30) Foreign Application Priority Data

Jun. 16, 2009 (KR) ........................ 10-2009-0053383
Jun. 15, 2010 (KR) ........................ 10-2010-0056696

(51) Int. Cl.
*C12N 5/00* (2006.01)
*C12N 5/02* (2006.01)
*C12N 5/071* (2010.01)

(52) U.S. Cl.
USPC ........................... 435/384; 435/375; 435/366

(58) Field of Classification Search
None
See application file for complete search history.

(56) References Cited

U.S. PATENT DOCUMENTS 5,942,435 A * 8/1999 Wheeler ........................ 435/325
2003/0095956 A1 5/2003 Weiss et al.
2004/0082003 A1 4/2004 Sauvageau et al.

FOREIGN PATENT DOCUMENTS

WO WO-2008-043181 4/2008
WO WO-2008-129563 10/2008

OTHER PUBLICATIONS

Howell et al. "Neuropeptide Y stimulates neuronal precursor proliferation in the post-natal and adult dentate gyrus" J. of Neurochemistry 93(3): 560-70, 2005.*
Sato et al. (2004) Nat. Med. 10:55-63.*
Ginis I, et al., "Differences between human and mouse embryonic stem cells," Dev. Biol. 269:360-380 (2004).*
Forsyth N, et al., "Telomerase and differentiation in multicellular organisms: turn it off, turn it on, and turn it off again," Differentiation 69:188-197 (2002).*
Xu R, et al., "Basic FGF and suppression of BMP signaling sustain undifferentiated proliferation of human ESCs," Nat. Methods 2:185-190 (2005).*
Odorico J, et al., "Multilineage differentiation from human embryonic stem cell lines," Stem Cells 19:193-204 (2001).*
J. Neurochem., 2005, vol. 93, pp. 560-570, Howell et al.
International Search Report, dated Mar. 22, 2011, for related application PCT/KR2010/003891.
Written Opinion of the International Searching Authority, dated Mar. 22, 2011, for related application PCT/KR2010/003891.
Takahashi, et al., "Induction of Pluripotent Stem Cells from Mouse Embryonic and Adult Fibroblast Cultures by Defined Factors", *Cell* 126, 663-676, Aug. 25, 2006.
Yoshida, et al., "Hypoxia Enhances the Generation of Induced Pluripotent Stem Cells", *Cell Stem Cell* 5, 237-241, Sep. 4, 2009.
Huangfu, et al., "Induction of pluripotent stem cells by defined factors is greatly improved by small-molecule compounds", *Nature Biotechnology*, vol. 26, No. 7, 795-797, Jul. 2008.
Assou, et al., "A Meta-Analysis of Human Embryonic Stem Cells Transcriptome Integrated into a Web-Based Expression Atlas", *Stem Cells* 2007, 25:961-973.
Takahashi, et al., "Induction of Pluripotent Stem Cells from Adult Human Fibroblasts by Defined Factors", *Cell* 131, 861-872, Nov. 30, 2007.
Hochedlinger, et al., "Nuclear reprogramming and pluripotency", *Nature*, vol. 441, 1061-1067, 2006.
Park, et al., "Reprogramming of human somatic cells to pluripotency with defined factors", *Nature*, vol. 451, 141-147, Jan. 10, 2008.

* cited by examiner

*Primary Examiner* — Valarie Bertoglio
(74) *Attorney, Agent, or Firm* — Sunstein Kann Murphy and Timbers LLP

(57) ABSTRACT

The present invention relates to a medium composition comprising neuropeptide Y, effective for proliferation and maintenance of undifferentiated pluripotent stem cells, and a method for culturing undifferentiated pluripotent stem cells using the same. The present invention improves the culture conditions for undifferentiated pluripotent stem cells, and ultimately, the present invention can be effectively used for the development of large-scale culture systems, thereby acquiring clinically applicable pluripotent stem cells. Further, the present invention relates to a dedifferentiation medium composition comprising neuropeptide Y (NPY), and a method for inducing dedifferentiation (or reprogramming) using the same. The present invention improves the culture conditions for dedifferentiation and contributes to develop technology of producing clinically applicable induced pluripotent stem cells, thereby being used for the development of stem cell therapy.

8 Claims, 30 Drawing Sheets

(1a)

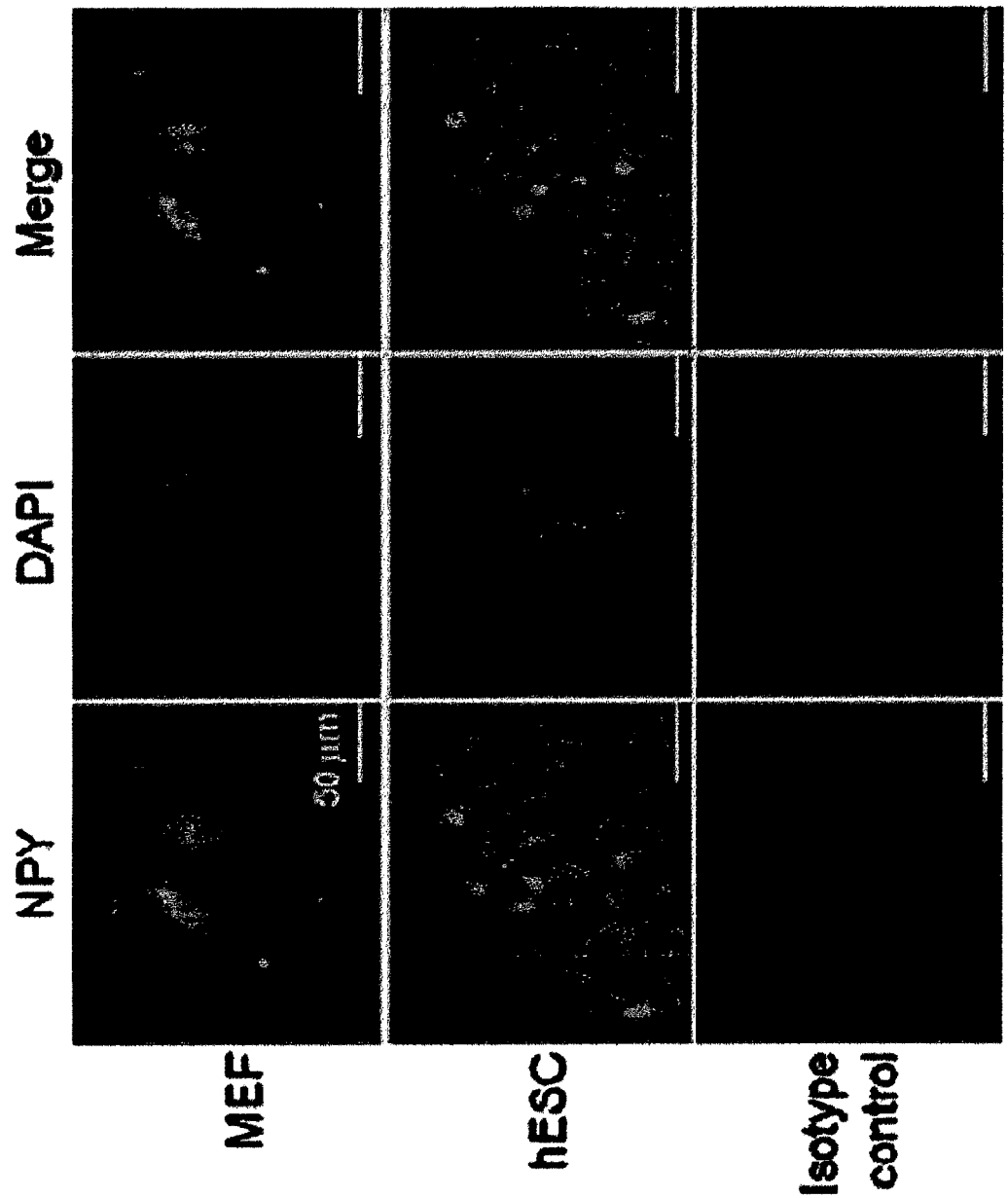

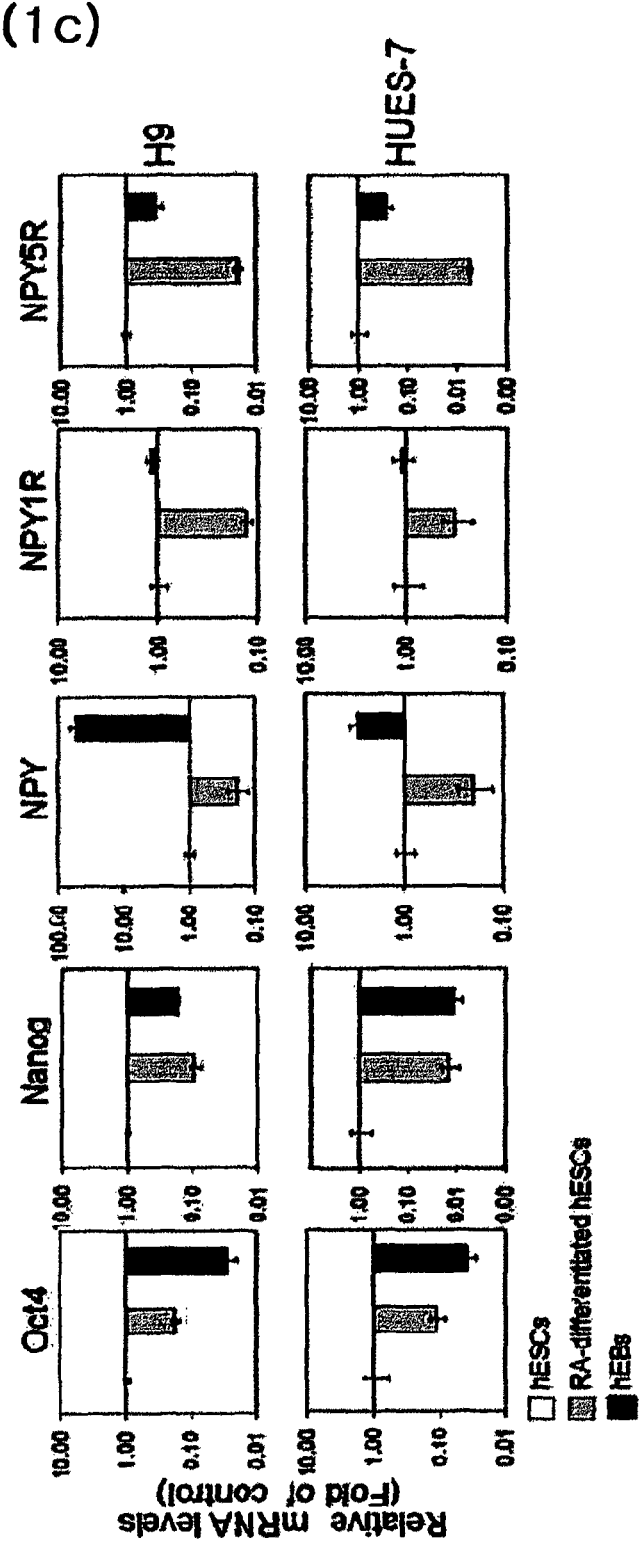

(2a)

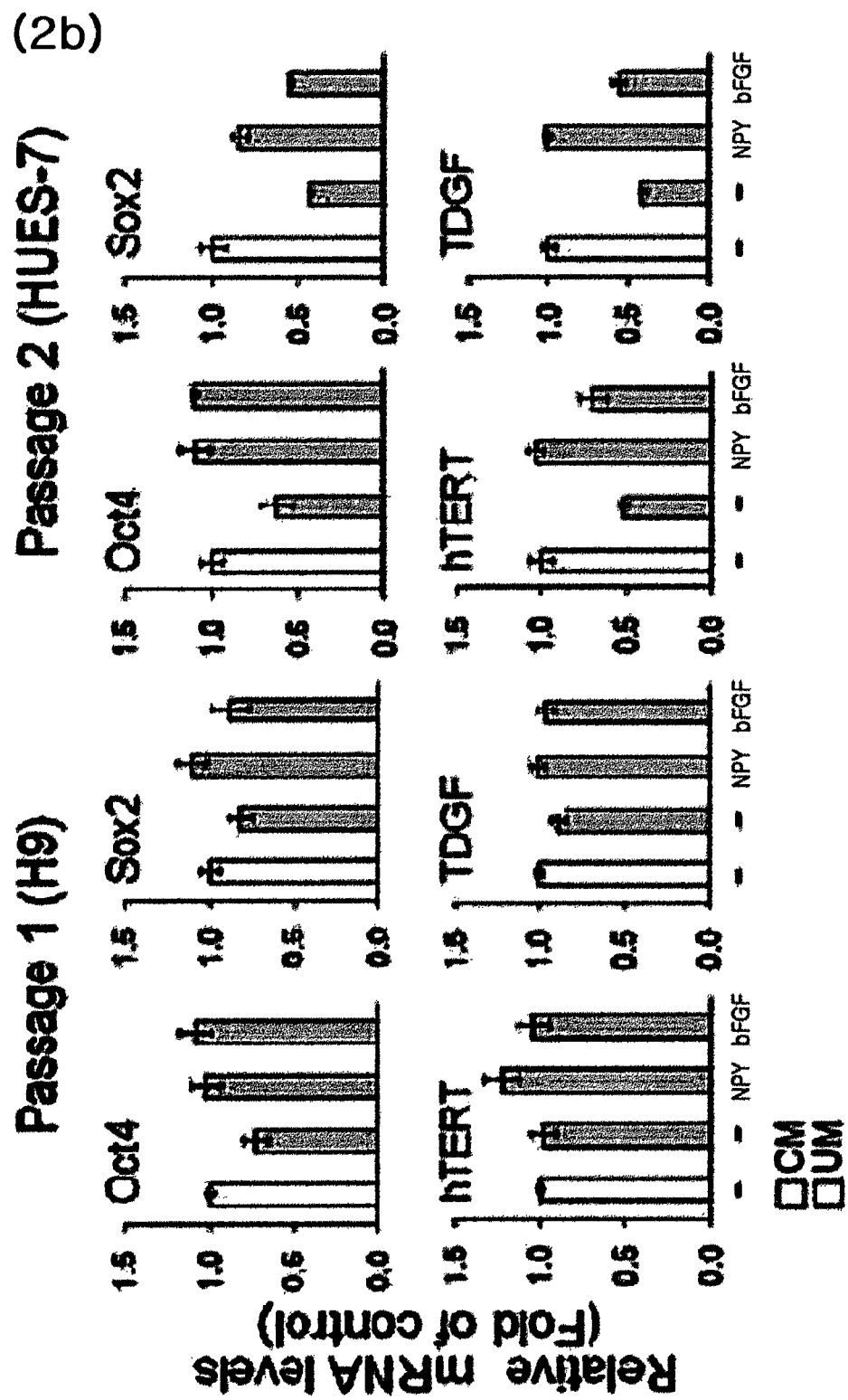

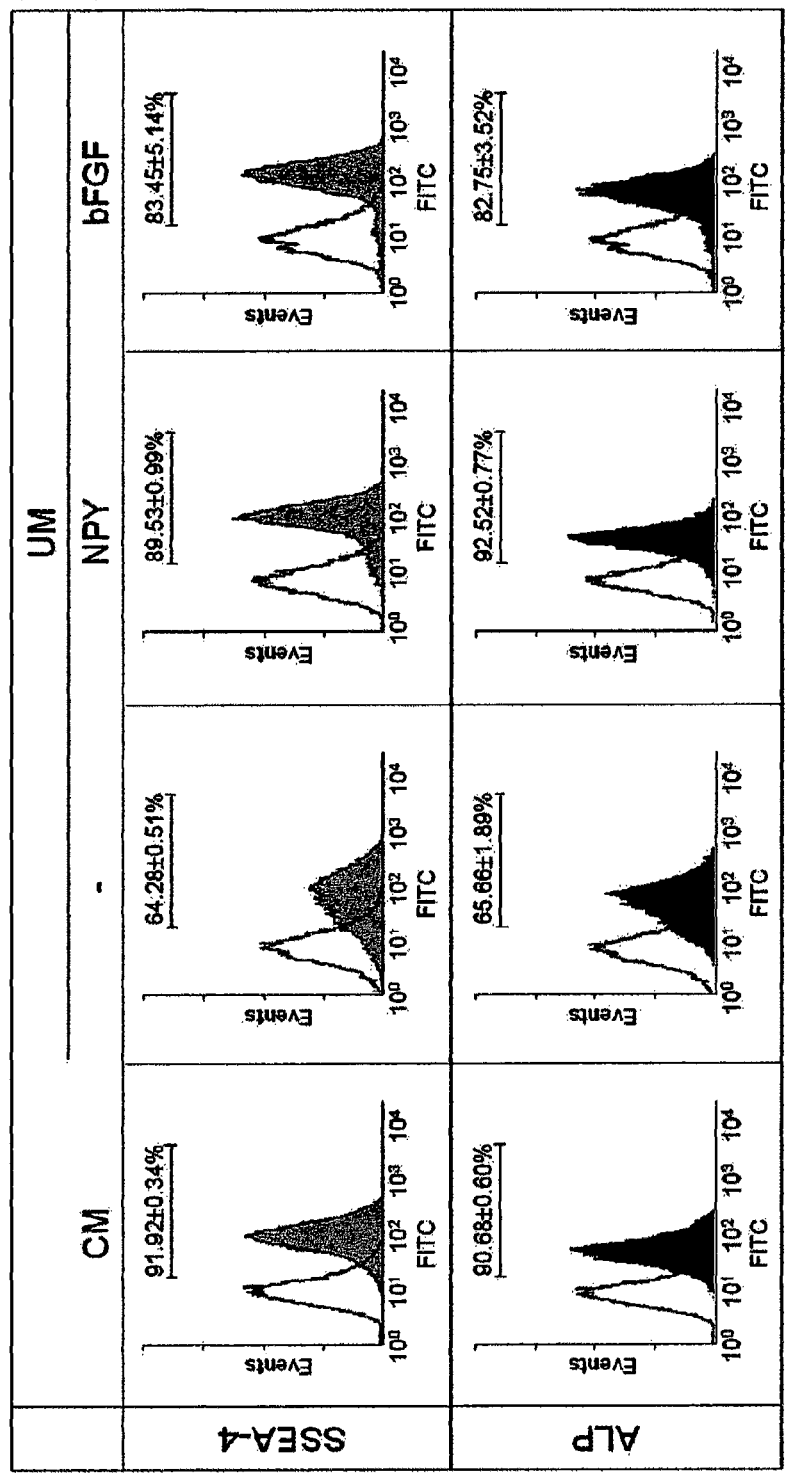

(3a)

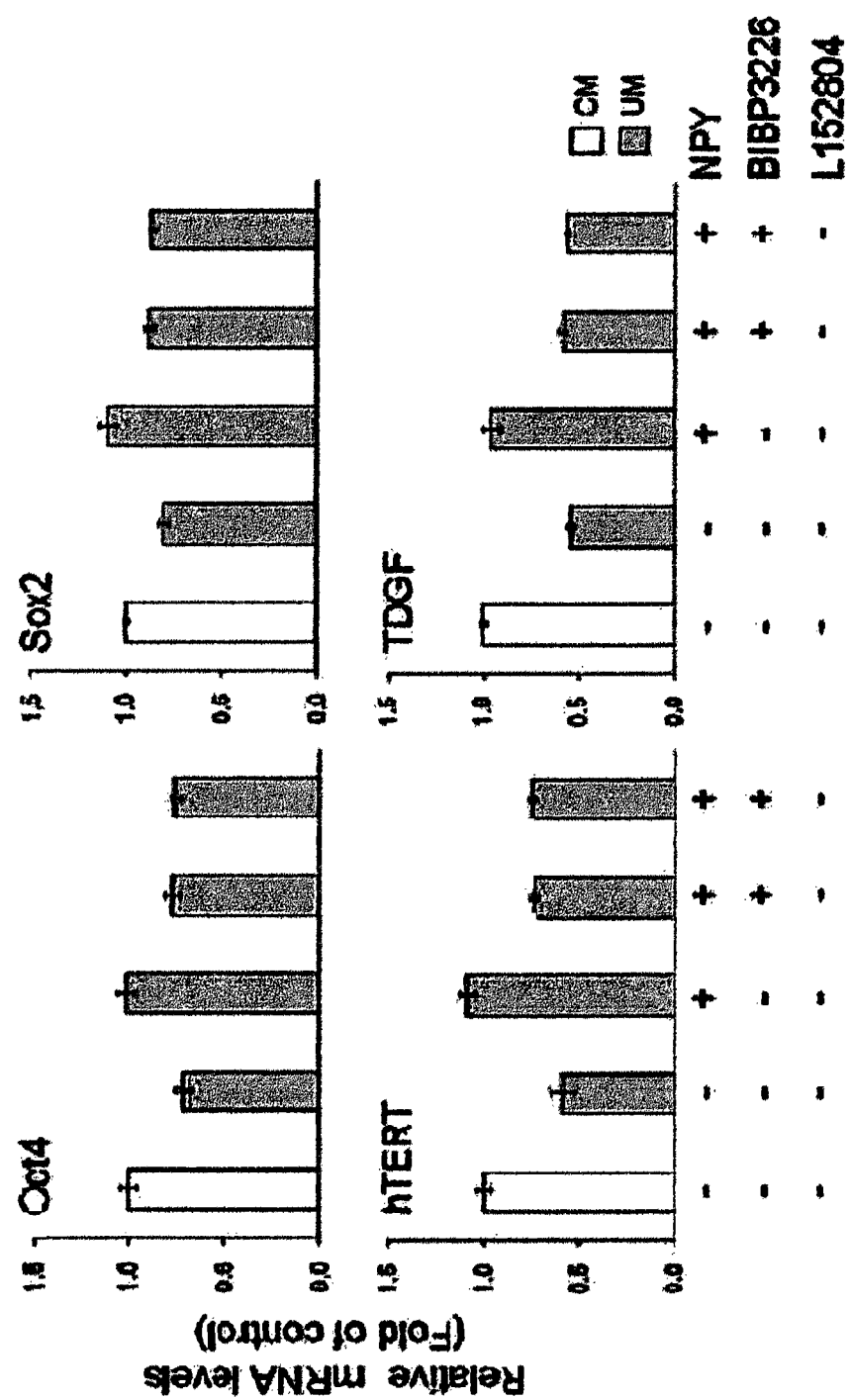

(4a)

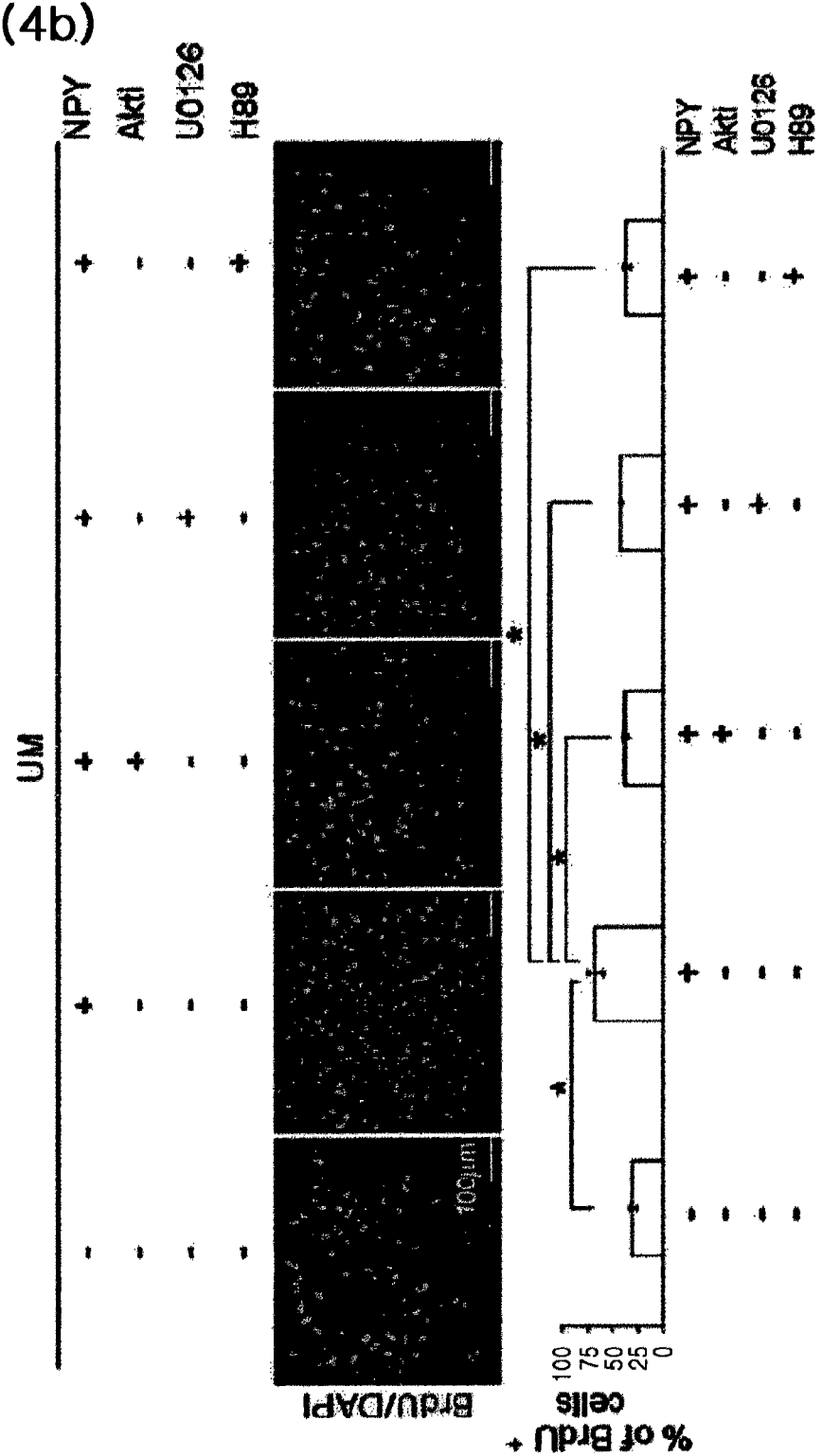

H9

| Medium conditions | Morphology | AP staining | Growth |
| --- | --- | --- | --- |
| CM | ++++ | ++++ | +++++ |
| N2B27 + 20ng/ml bFGF | ++ | ++ | +++ |
| N2B27+ 20ng/ml bFGF + 1µM NPY | +++ | ++++ | ++++ |
| N2B27+ 20ng/ml bFGF + 1ng/ml TGFβ | +++ | +++ | +++ |
| N2B27+ 20ng/ml bFGF + 1ng/ml TGFβ + 1µM NPY | ++++ | ++++ | ++++ |
| UM | + | + | ++ |
| UM + 1µM NPY | ++++ | ++++ | ++++ |

RT-PCR for trans gene confirmation of genomic DNA

MEDIUM COMPOSITION COMPRISING NEUROPEPTIDE Y FOR THE GENERATION, MAINTENANCE, PROLONGED UNDIFFERENTIATED GROWTH OF PLURIPOTENT STEM CELLS AND METHOD OF CULTURING PLURIPOTENT STEM CELL USING THE SAME

CROSS-REFERENCE TO RELATED APPLICATION

This application is the U.S. national phase application, pursuant to 35 U.S.C. §371, of PCT international application Ser. No. PCT/KR2010/003891, filed Jun. 16, 2010, designating the United States, which claims the benefit of Korean Application No. 10-2009-0053383, filed on Jun. 16, 2009, and Korean Application No. 10-2010-0056696, filed on Jun. 15, 2010. The entire contents of the aforementioned patent applications are incorporated herein by this reference.

SEQUENCE LISTING

The instant application contains a Sequence Listing which has been submitted in ASCII format via EFS-Web and is hereby incorporated by reference in its entirety. Said ASCII copy, created on Dec. 14, 2011, is named Seq_Listing.txt and is 9,787 bytes in size.

TECHNICAL FIELD

The present invention relates to a culture medium composition comprising neuropeptide Y (NPY) which is effective for undifferentiated growth and maintenance of pluripotent stem cells, and a method for culturing undifferentiated pluripotent stem cells using the same. More particularly, neuropeptide Y is used as a culture medium composition for undifferentiated pluripotent stem cells to effectively proliferate and culture pluripotent stem cells in an undifferentiated state. In particular, neuropeptide Y was found to support the long-term culture of undifferentiated pluripotent stem cells without feeder cell-derived factors or animal serum for several serial passages, almost to a similar extent as pluripotent stem cells co-cultured with feeder cells or cultured in feeder cell-conditioned medium. In addition, the present invention relates to a dedifferentiation (or reprogramming) medium composition comprising neuropeptide Y (NPY), and a method for inducing dedifferentiation using the same. More particularly, when neuropeptide Y is added to a medium composition during the dedifferentiation process, the efficiency of dedifferentiation can be significantly improved and the induced pluripotent stem cells produced by the method were found to have properties of pluripotent stem cells.

BACKGROUND ART

Stem cells refer to cells that can proliferate indefinitely in an undifferentiated state as well as differentiate into certain specific cell types under the effect of appropriate stimuli or environments. Since human pluripotent stem cells are able to proliferate indefinitely under in vitro culture conditions (self-renewal) and differentiate into nearly all cell types of an individual (pluripotency), findings in the studies of human pluripotent stem cells are utilized in a wide variety of fields, including basic studies for understanding the development, differentiation and growth of an individual, development of cell therapy products for the treatment of damages or various diseases of an individual, and efficacy screening for candidate therapeutic drugs, disease etiology study, and development of therapy strategies. Even though the demand for human pluripotent stem cells is rapidly increasing in a variety of fields, there is an obstacle to the use of such cells in the development of the related technology because culture media for maintenance and culture of undifferentiated human pluripotent stem cells are limited and the culture of pluripotent stem cells is difficult and laborious. In particular, for the development of cell therapy, it is necessary to establish clinically applicable culture conditions such as serum-free medium devoid of animal-derived products and develop large-scale culture systems capable of supplying them at a sufficient amount when needed.

Usually, human pluripotent stem cells can be maintained and cultured in an undifferentiated state by co-culturing with feeder cells such as mouse embryonic fibroblast (MEF) or culturing in feeder cell-conditioned medium (CM). When human pluripotent stem cells are co-cultured with feeder cells or cultured in feeder cell-conditioned medium, unfortunately, there is the risk of cross-transfer of one or more pathogens such as virus from the xenogeneic feeders.

Recently, many studies have been made to develop a method for culturing human pluripotent stem cells without feeder cells and with defined factors only. To achieve this, it is important to develop methods of maintaining and proliferating stem cells in an undifferentiated state. The Xu group (Nat Biotechnol 18:399, 2000) established a feeder-free culture system using mouse embryonic fibroblast-derived CM and matrices such as laminin and matrigel. Further, Rosier (Bev Dyn 229:259, 2004) succeeded in maintaining human embryonic stem cells in a feeder-free condition for one year or longer by taking advantage of the CM established by the Xu group. However, such a CM suffers from a disadvantage in that a mouse-derived component is retained in the medium. In 2005, Xu et al. reported that undifferentiated human stem cells can be maintained in the absence of feeder cells by using bFGF in combination with other growth factors (STEM CELLS 23:315, 2005) or by adding an inhibitor of bFGF and BMP signaling pathway, noggin to the culture media without a conditioned medium (CM). It was also reported by Sato et al. that undifferentiated human embryonic stem cells could be maintained through the activation of the Wnt pathway using the GSK-3-specific inhibitor BIO in the absence of feeder cells (Nat. Med. 10:55, 2004).

Since most embryonic stem cells derived from the inner cell mass are either left in frozen storage or destroyed, there are no legal problems. However, due to the fact that extraction of stem cells from an embryo may be considered to be the destruction of human life, the debate over stem-cell research incorporates ethical and religious considerations. Moreover, since stem cells are derived from embryos in limited supply, immune incompatibility between individuals can cause immune rejection of transplanted cells in cell therapy. One of the alternatives to overcome these problems is that induced pluripotent stem cells (iPSC) having properties similar to embryonic stem cells are produced from somatic cells by the use of dedifferentiation factors (Cell 126, 663-676, 2006; Cell 131, 861-872, 2007; Nature 441, 1061-1067, 2006; Nature 451, 141-146, 2008). This success is expected to improve technology for practical use of pluripotent stem cells in stem cell therapy. Induced pluripotent stem cells are advantageous in that the generation of induced pluripotent stem cells does not require embryos, and the use of cells extracted from a patient does not cause immune rejection, and thus it becomes a very valuable tool for practical use. To advance the present technology to practical levels, it is important to develop follow-on technologies which improve the accompanying disadvantages, namely, low dedifferentiation efficiency and tumorigenic potential due to the use of integrating viruses for iPSC induction.

In this connection, some methods for improving dedifferentiation efficiency are reported to control extracellular conditions or use supplements, in particular, small molecule compounds. Further, it was also reported that dedifferentiation efficiency is effectively increased under hypoxic conditions similar to those of embryonic stem cells (Cell Stem Cell, 5: 237-241, 2009). Dr. Ding's group (Shi et al., Cell Stem Cell, 2008) reported that small molecule compounds such as BIX-01294 (G9a histone methyltransferase inhibitor), BayK8644 (L-type calcium channel agonist), and RG108 (DNA methyltransferase inhibitor) are effective for enhancing dedifferentiation efficiency and Dr. Melto's group (Huangfu et al., Nat Biotechnol, 2008) reported that small molecule compounds such as VPA (histone deacetylase inhibitor), TSA (histone deacetylase inhibitor), and SAHA (histone deacetylase inhibitor) are effective for enhancing dedifferentiation efficiency. There are suggested alternatives to the use of a virus: 1) transient expression of a single nonviral polycistronic vector (Gonzalez et al, PNAS USA, 2009; Chang at al, Stem cells, 2009), 2) application of an adenovirus (Stadtfeld at al, Science 2008), and 3) Cre/loxP recombinant expression control system (Soldner et al, Cell, 2009), iPSC establishment using a single nonviral polycistronic vector and removal of dedifferentiation cassette by Cre transfection (kaji at al, Nature, 2009), 4) piggyback (PB) transposon system (Woltjen et al, Nature, 2009; kaji et al, Nature, 2009), and 5) nonintegrating episomal vectors (Yu et al, Science, 2009). Nevertheless, there still remain the problems of genetic abnormalities and tumorigenic potential.

Neuropeptide Y (NPY) is a 36 amino-acid peptide which, together with pancreatic polypeptide (PP), belongs to a family of neuroendocrine peptides. The peptide is widely distributed throughout the central and peripheral nervous system of mammals, and in particular, is abundant in the hypothalamus and cerebral cortex. It is known that NPY exerts a remarkably wide variety of physiological effects of potential therapeutic importance, and induces vasoconstriction when administered alone, and can cause angina pectoris (Clarke, et al., Lancet 1(8541):1057 (1987)). In addition, NPY, which is a neurotransmitter distributed throughout the central and peripheral nervous system, stimulates appetite and decreases energy expenditure during starvation. For example, when injected into the brain, NPY increases appetite in various species, and chronically causes an increase in body weight and insulin resistance. In particular, NPY modulates leptin actions in the hypothalamus. Leptin- and leptin receptor-deficient rodents have increased hypothalamic NPY, whereas NPY deficiency makes leptin-deficient mice less obese. Even though NPY has such a variety of physiological actions, there have been no studies on the actions and use of NPY in human pluripotent stem cells.

DISCLOSURE

Technical Problem

Therefore, the present inventors confirmed that a medium composition comprising exogenous NPY effectively supports the long-term maintenance and culture of undifferentiated pluripotent stem cells and culture technology of pluripotent stem cells can be remarkably improved by a culture method using the same. Further, the present inventors confirmed that the medium composition comprising exogenous NPY effectively supports induction of dedifferentiation during the dedifferentiation (or reprogramming) process and remarkably improves dedifferentiation (or reprogramming) efficiency. They also found that the induced pluripotent stem cells produced by the method have properties of embryonic stem cells, thereby completing the present invention.

Solution to Problem

It is an object of the present invention to provide a medium composition comprising neuropeptide Y, capable of effectively maintaining and culturing undifferentiated pluripotent stem cells in the presence or absence of animal serum or feeder cell-derived factors.

It is another object of the present invention to provide pluripotent stem cells cultured in the medium composition which comprises neuropeptide Y to culture undifferentiated pluripotent stem cells in the absence of animal serum or feeder cell-derived factors, and an in vitro cell culture.

It is still another object of the present invention to provide a method for establishing undifferentiated pluripotent stem cell lines, comprising the step of obtaining pluripotent stem cells under culture conditions including the above medium composition comprising neuropeptide Y.

It is still another object of the present invention to provide a method for culturing undifferentiated pluripotent stem cells in the medium composition comprising neuropeptide Y in the absence of feeder cell-derived factors using defined factors only without being contaminated by xeno-factors through several serial passages.

It is still another object of the present invention to provide a dedifferentiation medium composition comprising neuropeptide Y (NPY).

It is still another object of the present invention to provide a method for inducing dedifferentiation, comprising the step of culturing differentiated cells in the medium composition comprising neuropeptide Y.

It is still another object of the present invention to provide a method for establishing dedifferentiated cell lines, comprising the step of dedifferentiating differentiated cells under culture conditions including the above medium composition comprising neuropeptide Y.

It is still another object of the present invention to provide an in vitro cell culture comprising differentiated cells and the medium composition comprising neuropeptide Y, in which the differentiated cells are dedifferentiated.

Advantageous Effects of Invention

The medium composition comprising neuropeptide Y (NPY) according to the present invention, capable of inducing undifferentiated growth of pluripotent stem cells, is able to support the long-term maintenance and culture of undifferentiated pluripotent stem cells without feeder cell-derived factors or animal serum (xeno-factors), and improve the dedifferentiation efficiency and culture conditions for dedifferentiation when used during the dedifferentiation process. In addition, the culture method using the medium composition can be effectively used for the development of a clinically applicable culture method of pluripotent stem cells as well as large-scale culture systems for pluripotent stem cells including embryonic stem cells and induced pluripotent stem cells.

BEST MODE FOR CARRYING OUT THE INVENTION

In one aspect to achieve the above objects, the present invention provides a medium composition for pluripotent stem cells used for maintenance and culture of undifferentiated pluripotent stem cells, which comprises neuropeptide Y sufficient to maintain and culture the properties of the undifferentiated pluripotent stem cells.

As used herein, the term 'neuropeptide Y (NPY)' refers to a peptide that consists of 36 amino acids and is structurally related with pancreatic polypeptide (PP). It is known to be mainly distributed in the nervous system. The peptide has 50% sequence homology with PP produced in pancreatic cells, and 69% sequence homology with PYY (Peptide YY) produced in nerve cells, and thus they are often said to belong to the "pp family". NPY exhibits a variety of physiological actions in motility and secretory functions of the gastrointestinal tract, such as inhibitions of gastric acid secretion, gastric emptying, pancreatic exocrine secretion, and insulin and glucagon secretion.

In accordance with one specific embodiment of the present invention, the medium composition may contain neuropeptide Y in the range from 0.01 to 100 μM, and more preferably from 0.1 to 10 μM.

Figure 1:
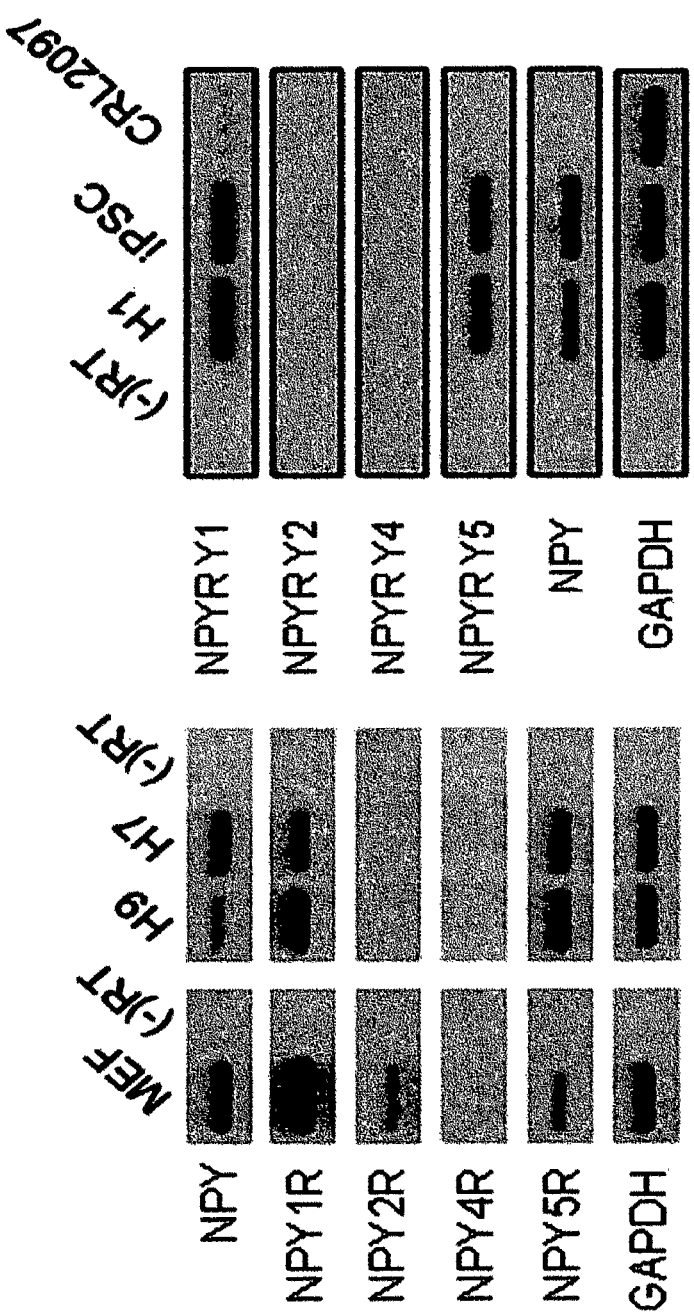
FIG. 1 shows expression of NPY and its receptor subtypes on human embryonic stem cells (hESCs), human induced pluripotent stem cells (hiPSCs) and mouse embryonic fibroblasts (MEFS) feeder cells. (a) Semi-quantitative RT-PCR analysis of mRNA expression for NPY, NPY Y1, NPY Y2, NPY Y4 and NPY Y5 in hESCs (H9, HEUS-7, and H-1), hiPSCs, and MEFs. GAPDH was used as a loading control. (b) Immunofluorescent analysis of NPY protein expression in H9 cells and MEFs. Cell nuclei were counterstained with DAPI. Bar=50 μm. (c) Real-time qRT-PCR analysis of mRNA expression of NPY, NPY Y1 and NPY Y5 in undifferentiated and differentiated H9 hESCs (RA-differentiated hESCs and differentiating hEBs). The results are displayed as the relative mRNA level with the level in undifferentiated hESCs cultured in the MEF-CM referred set to 1 and are presented as the mean±SE (n=3).

Meanwhile, as used herein, the term 'neuropeptide Y receptor' is closely related with NPY in terms of their various functions. Up to now, there have been known six NPY receptors (Y1, Y2, Y3, Y4, Y5 and Y6), and mammals have five subtypes of NPY receptors, Y1, Y2, Y4, Y5 and Y6, which belong to the G protein coupled receptor (GPCR) superfamily. Each receptor functions differently depending on its location and distribution. The receptor Y1 exists in the myenteric plexus of mammals, such as rabbit, guinea pig, rat, and human, and also in the smooth muscle, together with Y2. NPY used in the present invention was purchased from sigma. In the specific embodiment of the present invention, expression of NPY and its receptors in human embryonic stem cells, human induced pluripotent stem cells and mouse embryonic fibroblast (MEF) feeder cells was confirmed at a gene level (FIG. 1a), and NPY expression in both the nuclei and cytoplasm of human embryonic stem cells and MEF was confirmed at a protein level (FIG. 1b).

As used herein, the term 'pluripotent stem cells' refer to stem cells having self-renewal capacity, being pluripotent or totipotent, which are able to differentiate into any cell type of an individual, and embrace embryonic stem cells and induced pluripotent stem cells, but are not limited thereto.

As used herein, the term 'embryonic stem cells' refer to cells, derived from the inner cell mass of blastocysts at a stage before it would implant in the uterine wall, having self-renewal capacity and being pluripotent or totipotent, which are able to differentiate into any cell type of an individual, and embraces embryoid bodies derived from embryonic stem cells. Usable in the present invention are embryonic stem cells derived from any animal including humans, monkeys, pigs, horses, cows, sheep, dogs, cats, mice, rabbits, etc., with preference for humans.

As used herein, the term 'induced pluripotent stem cells' refers to cells that have been induced to have pluripotency from differentiated cells by stimulation of dedifferentiation, so called iPSC. The dedifferentiation process can be performed by using a viral-mediated vector such as retrovirus and lentivirus or a non viral-mediated vector, or by introduction of non viral-mediated dedifferentiation factors using proteins and cell extracts, and includes dedifferentiation process by stem cell extracts, compounds or the like. Induced pluripotent stem cells have properties almost similar to those of embryonic stem cells, and specifically, show similarity in cell morphology and expression patterns of gene and protein, have pluripotency in vitro and in vivo, form teratomas, and generate chimeric mouse and germline transmission after blastocyst injection. Usable in the present invention are induced pluripotent stem cells derived from any animal including humans, monkeys, pigs, horses, cows, sheep, dogs, cats, mice, rabbits, etc., with preference for humans.

In one specific embodiment of the present invention, it was confirmed that human embryonic stem cells and human induced pluripotent stem cells maintained and cultured in unconditioned medium (UM) free of undifferentiation factors were induced to differentiate, whereas those cultured in UM supplemented with NPY were maintained in an undifferentiated state, indicating that NPY supports maintenance of undifferentiated human embryonic stem cells and human induced pluripotent stem cells.

Figure 2:
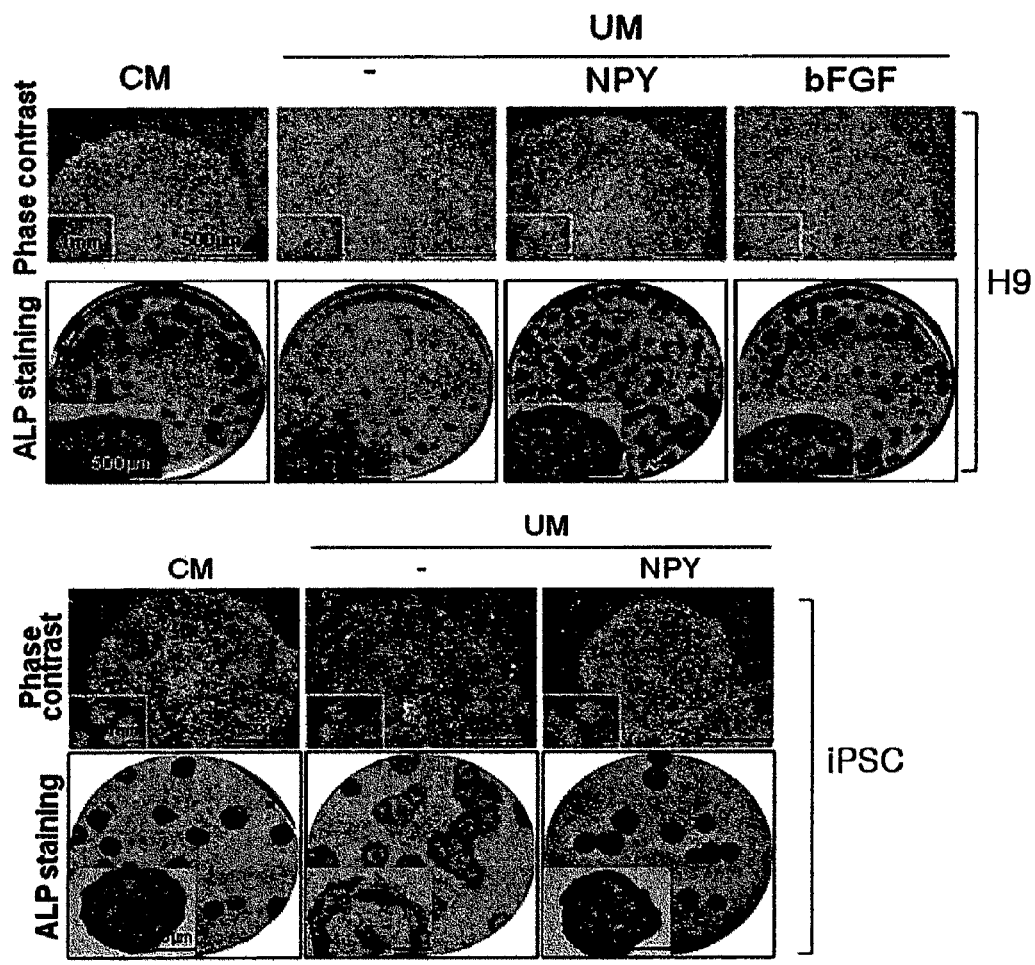
FIG. 2 shows culture results of hESCs and hiPSCs in feeder-free NPY medium. (a) Representative morphology of H9 hESCs and hiPSCs cultured in a MEF conditioned medium (CM) or unconditioned medium (UM) containing 0.5 μM NPY or 40 ng/ml bFGF for three passages. Upper panels: Phase contrast images. Bar=500 μm or 1 mm (inset images). Lower panels: Scanned images of 35 mm round culture dishes and inverted macroscopic images were acquired after ALP staining. Bar=500 μm (inset images). (b) Real-time qRT PCR analysis for the expression of OCT4, SOX2, hTERT and TDGF. H9 and HEUS-7 hESCs were cultured using the indicated media for one or two passages. The results are displayed as the relative mRNA level with the level detected in undifferentiated hESCs cultured in CM set to 1 and are presented as the mean±SE. (c) FACS analysis of SSEA-4 and ALP expression on H9 hESCs. Representative plots following flow cytometry from three independent experiments are shown.

More particularly, human embryonic stem cells cultured in UM underwent the early phases of differentiation, as indicated by changes in morphology being different from those of the undifferentiated state (FIG. 2a) and the down-regulation of hESC markers including alkaline phosphatase (ALP), OCT4, SOX2, human telomerase reverse transcriptase (hTERT), teratocarcinoma-derived growth factor (TDGF) and SSFA-4 (FIGS. 2b and c). In contrast, human embryonic stem cells cultured in UM supplemented with NPY (>0.1 μM) significantly maintained their undifferentiated state, as compared to those cultured in UM. In particular, the addition of 0.5 μM NPY to UM effectively supported the maintenance of typical undifferentiated cell morphology, almost to a similar extent as human embryonic stem cells cultured in CM or UM plus high amounts of bFGF (=40 ng/ml) (FIG. 2a), and the expression of hESC markers including ALP, SOX2, hTERT, and SSEA-4 was examined to confirm that NPY effectively supports maintenance of human embryonic stem cells in an undifferentiated state (FIGS. 2a, 2b and 2c). Like human embryonic stem cells, human induced pluripotent stem cells cultured in UM lost their undifferentiated state (FIG. 2a), but human induced pluripotent stem cells cultured in UM supplemented with NPY (>0.1 µM) significantly maintained their undifferentiated state, as characterized by the typical hESC morphology (FIG. 2a). Similar to human embryonic stem cells, human induced pluripotent stem cells cultured in UM supplemented with 0.5 µM NPY significantly maintained their undifferentiated state almost to a similar extent as cells cultured in CM, as characterized by the typical morphology and the expression of the hESC markers. This result indicates that the NPY of the present invention effectively supports maintenance of undifferentiated human induced pluripotent stem cells (FIG. 2a). Moreover, human embryonic stem cells cultured in UM lost their undifferentiated proliferation capacity (FIG. 4a), but those cultured in UM supplemented with NPY (>0.1 µM) maintained their undifferentiated proliferation capacity, almost to a similar extent as undifferentiated cells cultured in CM (FIG. 4a), as characterized by determining the number of BrdU+ cells. This result indicates that NPY contributes to undifferentiated proliferation and maintenance of human embryonic stem cells.

As used herein, the term 'feeder cell-derived factors' refer to factors derived from other cells that support undifferentiated proliferation of stem cells or from cell culture thereof, and mouse embryonic fibroblasts or human foreskin fibroblasts are usually used. When the feeder cells are used, unfortunately, proliferation of feeder cells may occur in addition to undifferentiated proliferation of pure stem cells, and there is the risk of cross-transfer of pathogens from the feeder cells and long-term growth of stem cells may be inhibited by their limited passage capacity. Therefore, the present inventors tested the functions of neuropeptide NPY as a novel growth factor for the improved culture of human pluripotent stem cells. They confirmed that NPY as a medium component effectively contributes to undifferentiated maintenance of human pluripotent stem cells under the culture conditions free of feeder cell-derived factors or animal serum.

As used herein, the term 'culture media' means media which assure the growth and survival of stem cells in vitro, and which may include all of the pertinent media typically used in the art. The culture media and conditions depend on the kind of stem cells. Preferable is a cell culture minimum medium (CCMM), which generally comprises a carbon source, a nitrogen source and trace elements. Examples of the CCMM include, but are not limited to, DMEM (Dulbecco's Modified Eagle's Medium), MEM (Minimal essential Medium), BME (Basal Medium Eagle), RPMI1640, F-10, F-12, aMEM (a Minimal essential Medium), GMEM (Glasgow's Minimal essential Medium), and Iscove's Modified Dulbecco's Medium.

In the specific embodiment of the present invention, the medium composition may further include one or more selected from the group consisting of N2 supplement, B27 supplement, bFGF and TGFβ without animal serum and feeder cell-derived factors. In this connection, the N2 and B27 supplements may be provided in a ratio of 1:1, and bFGF and TGFβ may be provided at a concentration of 4-40 ng/ml and 1-10 ng/ml, respectively.

Preferably, UM used in the present invention includes 80% DMEM/F12, 20% KSR, 1% NEAA, 1 mM L-glutamine, 0.1 mM 3-mercaptoethanol (Sigma) and 4 ng/ml bFGF, and for culture in the absence of feeder cell-derived factors and serum, human pluripotent stem cells are cultured in N2/B27-based medium containing DMEM/F12, 1×N2/B27 (Invitrogen), 1% NEAA, 1 mM L-glutamine, 0.1 mM β-mercaptoethanol with or without NPY and TGFβ (R&D systems, Minneapolis, Minn.) (Example 1).

Figure 15:
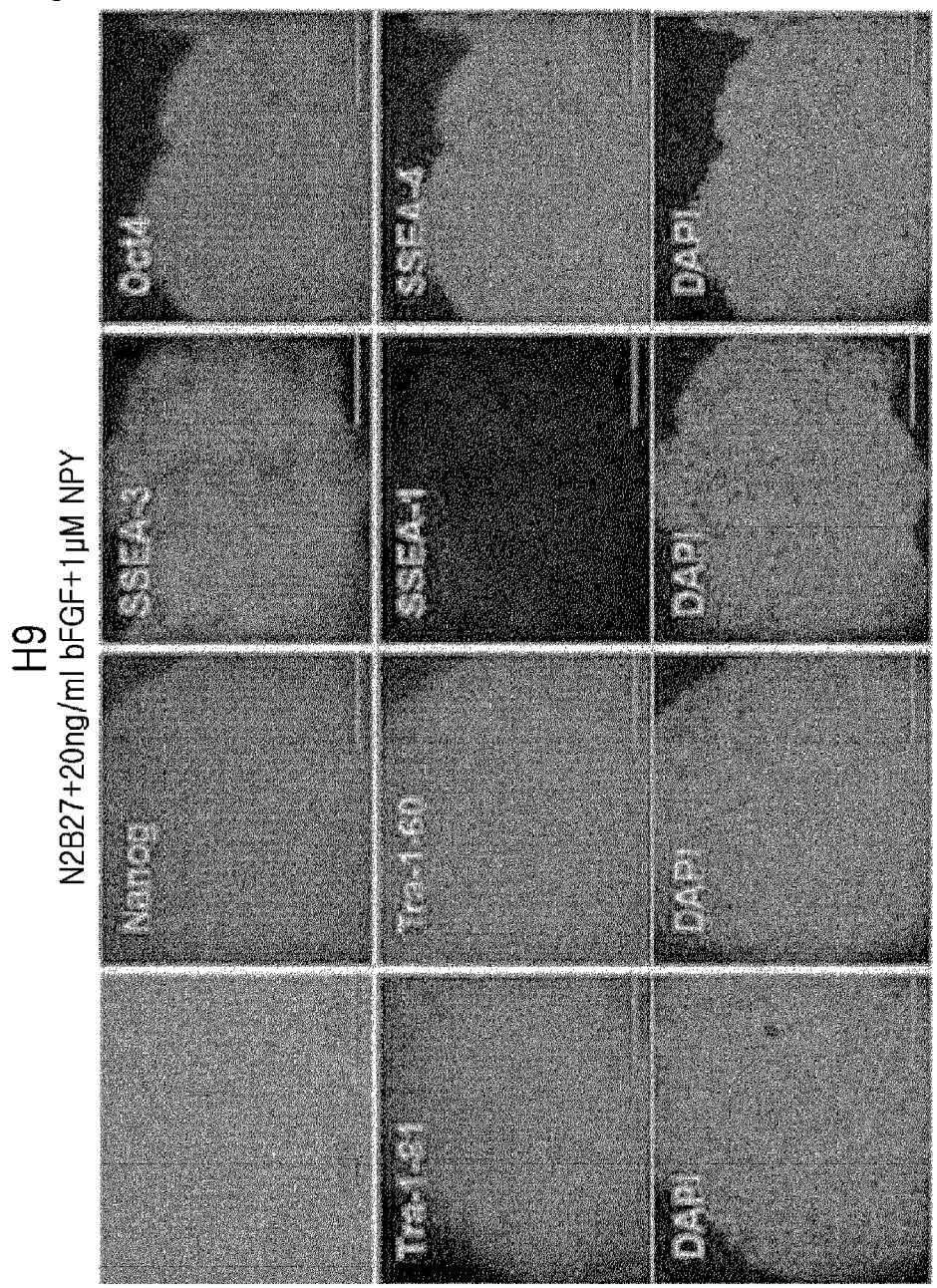
FIG. 15 shows a feeder-free, serum-free culture of hESCs in NPY-N2/B27 medium. Morphology of a representative hESC colony and immunohistochemical analysis of OCT4, NANOG, SSEA-1, SSEA-3, SSEA-4, TRA-1-60 and TRA-1-80. H9 cells were maintained in serum-free, feeder-free medium containing 1×DMEM/F12, 1×N2/B27, 1 μM NPY and 20 ng/ml bFGF for six passages. Nuclei were visualized with DAPI staining. Bar=500 μm or 1 mm (inset images).
Figure 16:
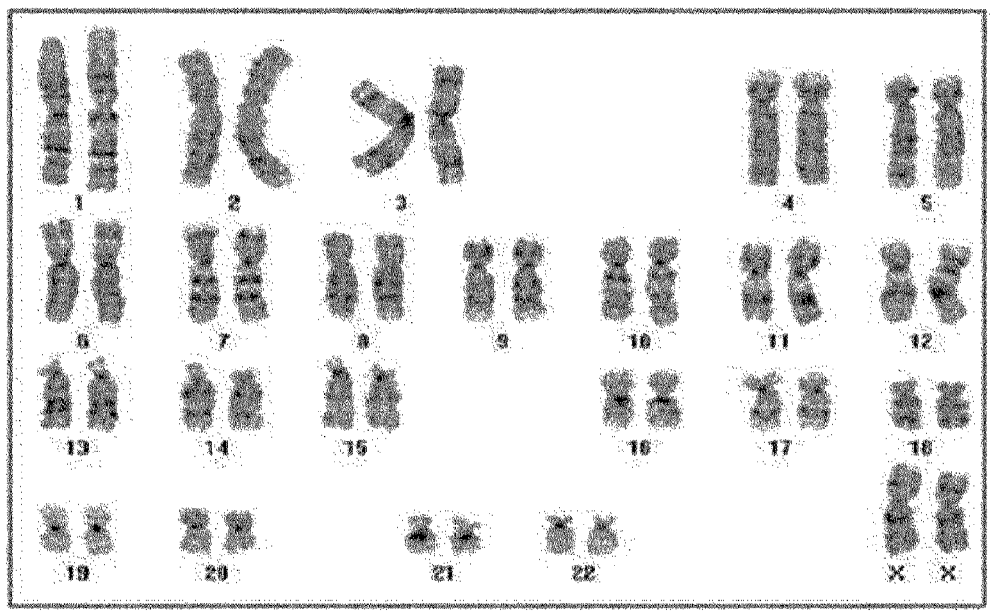
FIG. 16 shows a feeder-free, serum-free culture of hESCs in NPY-N2/B27 medium. Karyotype analysis of H9 cells cultured in NPY N2/B27 medium for six passages.
Figures 17, 18:
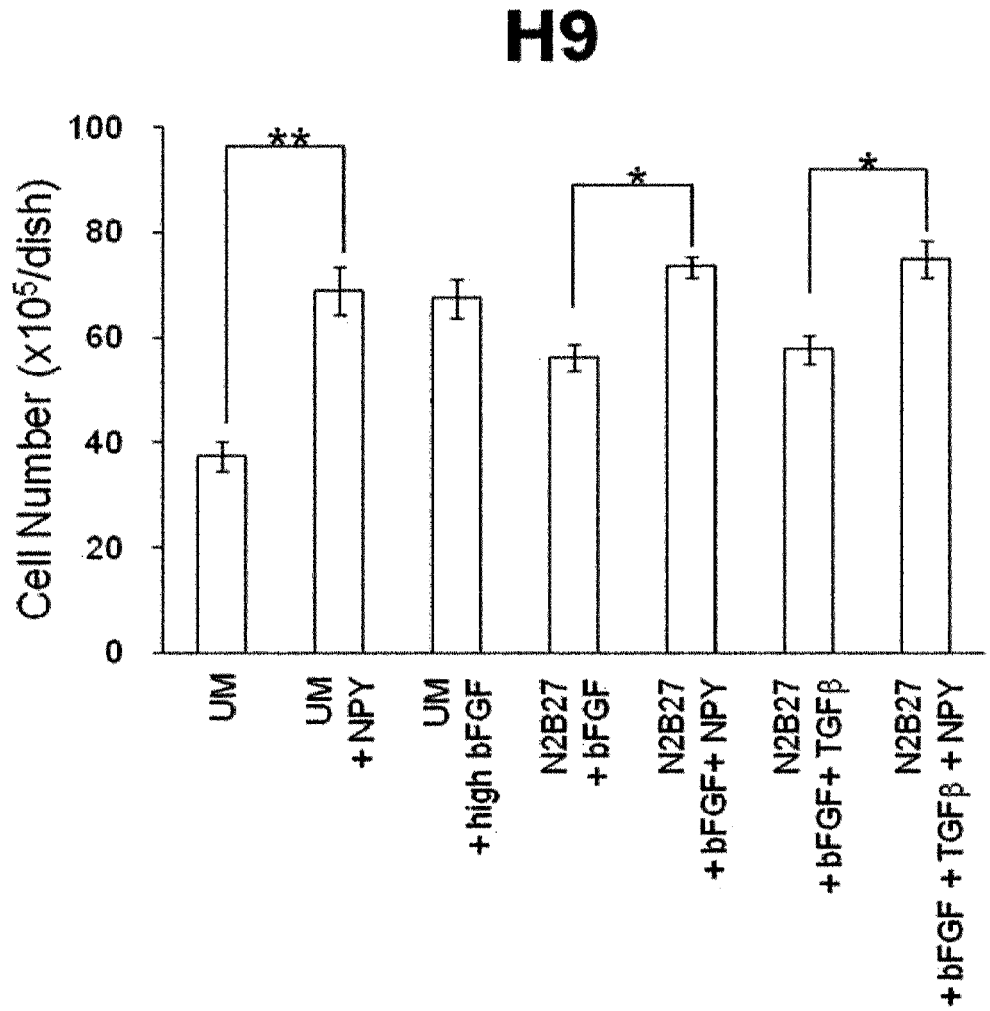
FIG. 17 shows a feeder-free, serum-free culture of hESCs in NPY-N2/B27 medium. Comparison of the growth efficiency of H9 cells cultured using the indicated media for 6 days by measuring the cell number as described in Materials and Methods. The data are presented as the mean±SE (n=3). **p<0.01, *p<0.02, by t-test.
FIG. 18 shows a feeder-free, serum-free culture of hESCs in NPY-N2/B27 medium. Comparison of different hESC culture conditions. hESCs cultured in different media were evaluated based on morphology, ALP staining and growth efficiency.

In the specific embodiment of the present invention, the addition of NPY (>0.1 µM) during long-term serial culture of human embryonic stem cells in N2, B27 supplement-based defined medium was found to effectively support undifferentiated maintenance, compared to that under the NPY-free conditions, which was confirmed by expression of undifferentiation-specific marker (FIG. 15), retained normal karyotype (FIG. 16) and increased undifferentiated growth efficiency (FIG. 17). In addition, combinatorial treatment of bFGF and TGFβ with NPY under the defined medium condition is efficient to support undifferentiated maintenance (FIG. 18).

As used herein, the term 'proliferation' means an increase in cell number, having the same meaning as 'growth'. By the term 'undifferentiated proliferation', as used herein, it is meant that pluripotent stem cells proliferate not into specific cells but into cells having the same properties as the pluripotent stem cells, that is, into pluripotent cells. It will be obvious to practitioners of the art that undifferentiated cells can be readily discerned from differentiated cells. For instance, morphologic features of undifferentiated cells are a high ratio of nucleus to cytoplasm and prominent nucleoli.

In another aspect, the present invention provides an in vitro cell culture comprising human embryonic stem cells, pluripotent stem cells containing human induced pluripotent stem cells, and a medium composition, the medium composition comprising neuropeptide Y in sufficient amount to maintain the pluripotent stem cells in an undifferentiated state for several serial passages, the medium composition being free of serum and feeder cell-derived factors and never having been exposed to serum or feeder cell-derived factors.

In this connection, usable in the present invention are pluripotent stem cells derived from any animal including humans, monkeys, pigs, horses, cows, sheep, dogs, cats, mice, rabbits, etc., with preference for humans.

In accordance with the specific embodiment of the present invention, the medium composition may include neuropeptide Y in the range from 0.01 to 100 µM, and more preferably from 0.1 to 10 µM.

In accordance with the specific embodiment of the present invention, the medium composition may further include one or more selected from the group consisting of N2 supplement, B27 supplement, bFGF and TGFβ without animal serum and feeder cell-derived factors. In this connection, the N2 and B27 supplements may be provided in a ratio of 1:1, and bFGF and TGFβ may be provided at a concentration of 4-100 ng/ml and 1-10 ng/ml, respectively.

In still another aspect, the present invention provides a method for establishing pluripotent stem cell lines in an undifferentiated state, comprising the step of obtaining pluripotent stem cells; and culturing the pluripotent stem cells under culture conditions including the above medium composition to obtain pluripotent stem cell lines.

In this connection, usable in the present invention are pluripotent stem cells derived from any animal including humans, monkeys, pigs, horses, cows, sheep, dogs, cats, mice, rabbits, etc., with preference for humans.

In still another aspect of the present invention, the present invention provides a method for culturing pluripotent stem cells in an undifferentiated state, comprising the step of culturing pluripotent stem cells in the medium composition comprising neuropeptide Y in sufficient amount to maintain the pluripotent stem cells in an undifferentiated state for several serial passages.

In this connection, the method is able to maintain pluripotent stem cells in an undifferentiated state with or without animal serum and feeder cell-derived factors.

In this connection, usable in the present invention are pluripotent stem cells derived from any animal including humans, monkeys, pigs, horses, cows, sheep, dogs, cats, mice, rabbits, etc., with preference for humans.

In the preferred embodiment of the present invention, the medium composition may contain neuropeptide Y in the range from 0.01 to 100 μM, and more preferably from 0.1 to 10 μM.

Further, in accordance with the specific embodiment of the present invention, the medium composition may further include one or more selected from the group consisting of N2 supplement, B27 supplement, bFGF and TGFβ without animal serum and feeder cells. In this connection, the N2 and B27 supplements may be provided in a ratio of 1:1, and bFGF and TGFβ may be provided at a concentration of 4-100 ng/ml and 1-10 ng/ml, respectively.

As used herein, the term 'passage' refers to a cell culture technique to transfer or transplant cells in fresh media every 5~7 days for preservation of cell lines, in particular, it is defined herein as the growth of pluripotent stem cells from an initial seed culture in a culture plate to growth to cell confluence in the same culture plate.

In accordance with the specific embodiment of the present invention, pluripotent stem cells can be maintained in an undifferentiated state over 15 passages without feeder cells.

Figure 6:
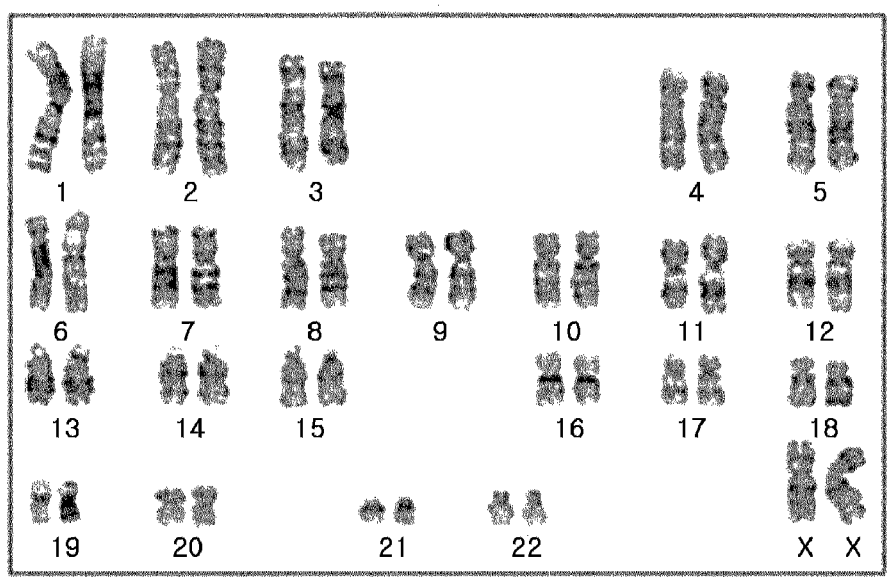
FIG. 6 shows a long-term culture of hESCs and hiPSCs in feeder-free NPY medium. Karyotype analysis of hESCs cultured in NPY medium for 15 passages.
Figure 6:
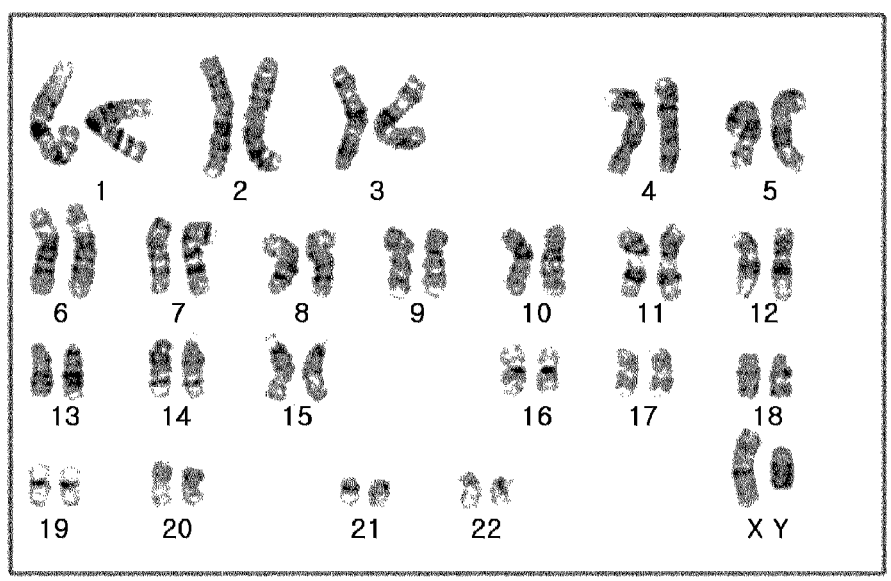
Figure 7:
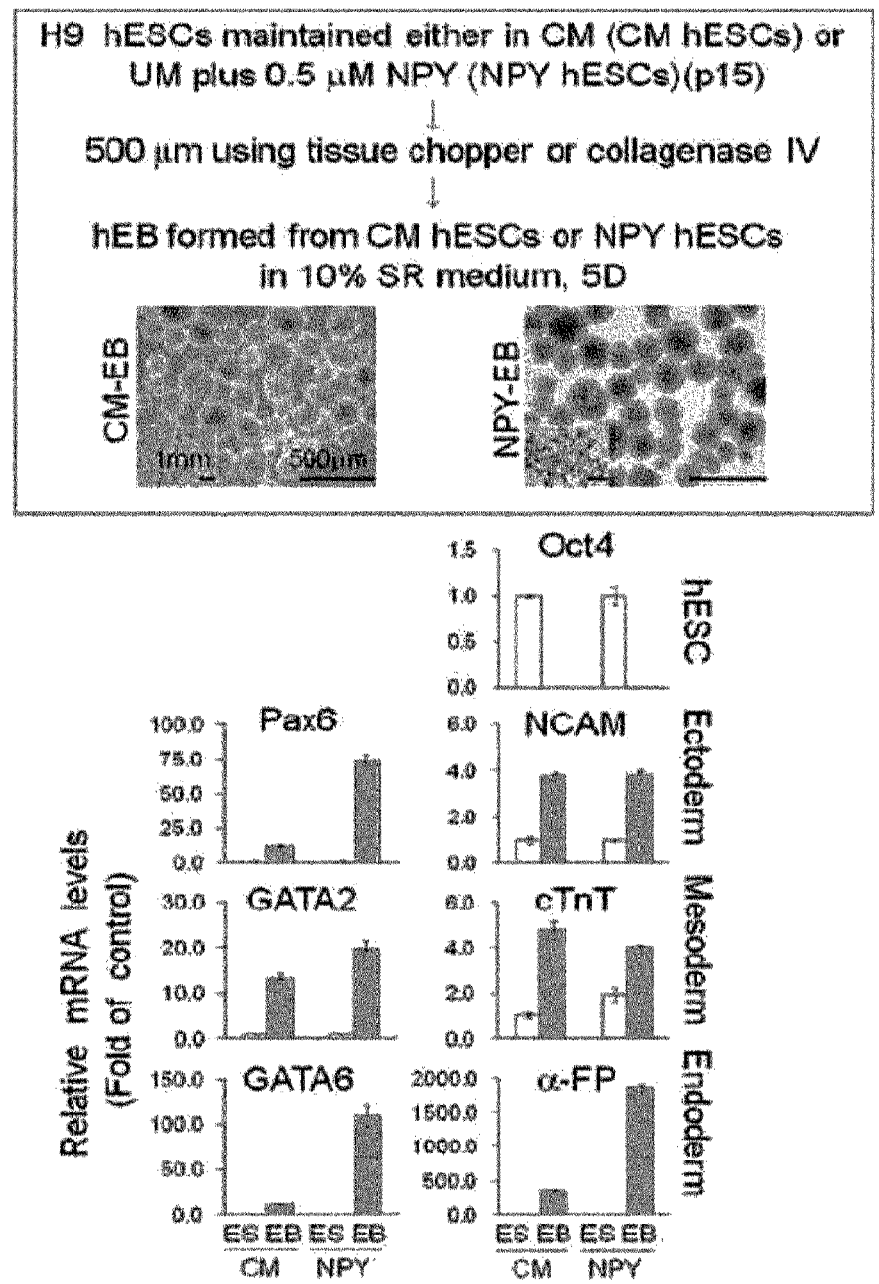
FIG. 7 shows a long-term culture of hESCs and hiPSCs in feeder-free NPY medium. Human embryoid body (hEB) formation and differentiation. hEBs derived from H9 cells were cultured in CM or NPY medium for 15 passages. Upper panel; Representative images of hEBs. Bar=500 μm or 1 mm (inset images). Lower panel; Real-time RT-PCR analysis for the expression of OCT4 and differentiation markers characteristic of the three-germ layers; ectoderm (PAX6 and NCAM), mesoderm (GATA2 and cTnT) and endoderm (α-FP and GATA6). The data are presented as the mean±SE of three independent experiments.
Figure 8:
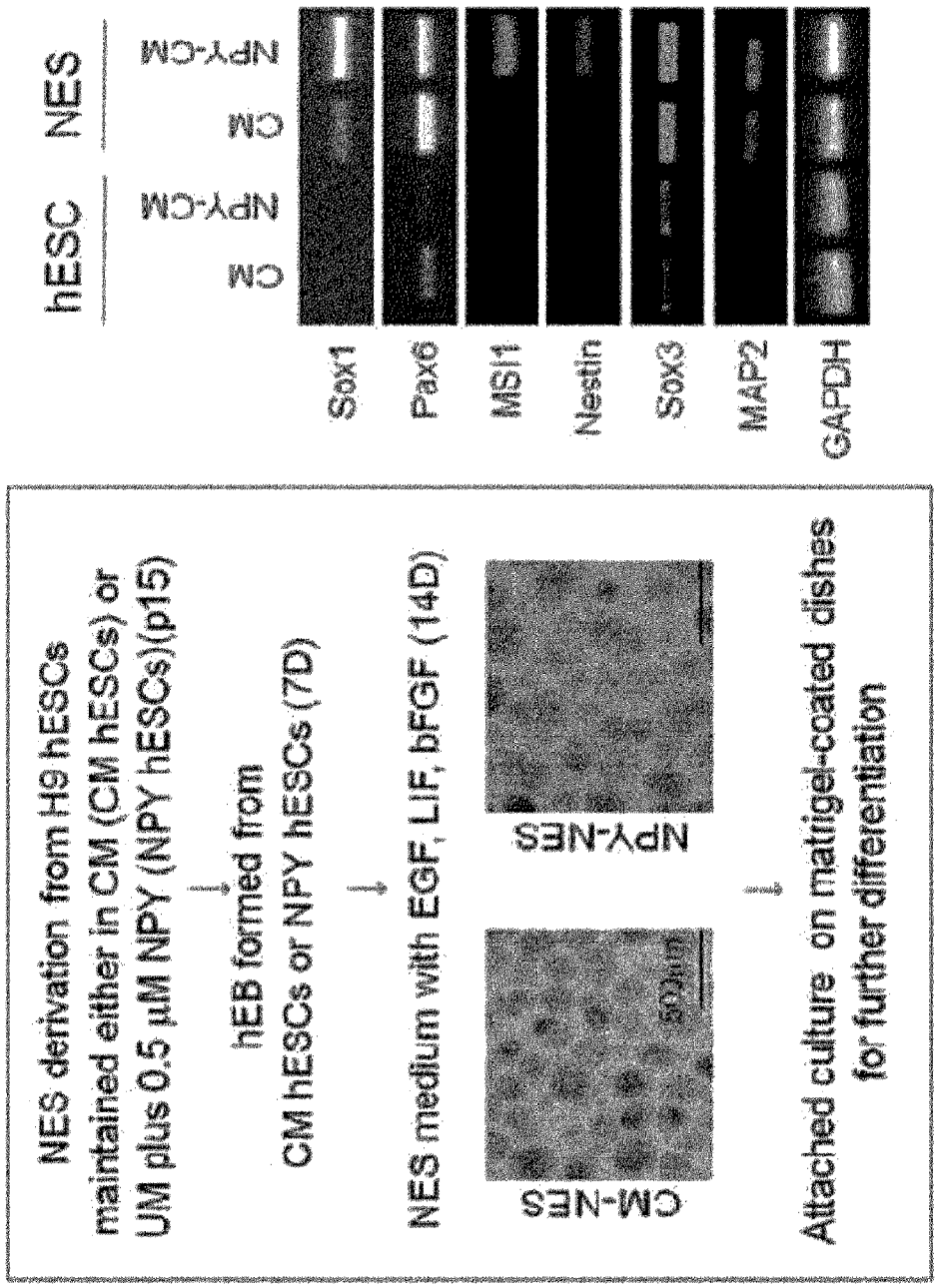
FIG. 8 shows a long-term culture of hESCs and hiPSCs in feeder-free NPY medium. Neuroectodermal spheres (NESs) derived from hESCs. Left panel; Representative images of NESs. Right panel; RT-PCR analysis of neural stem cell marker expression in NESs.
Figure 9:
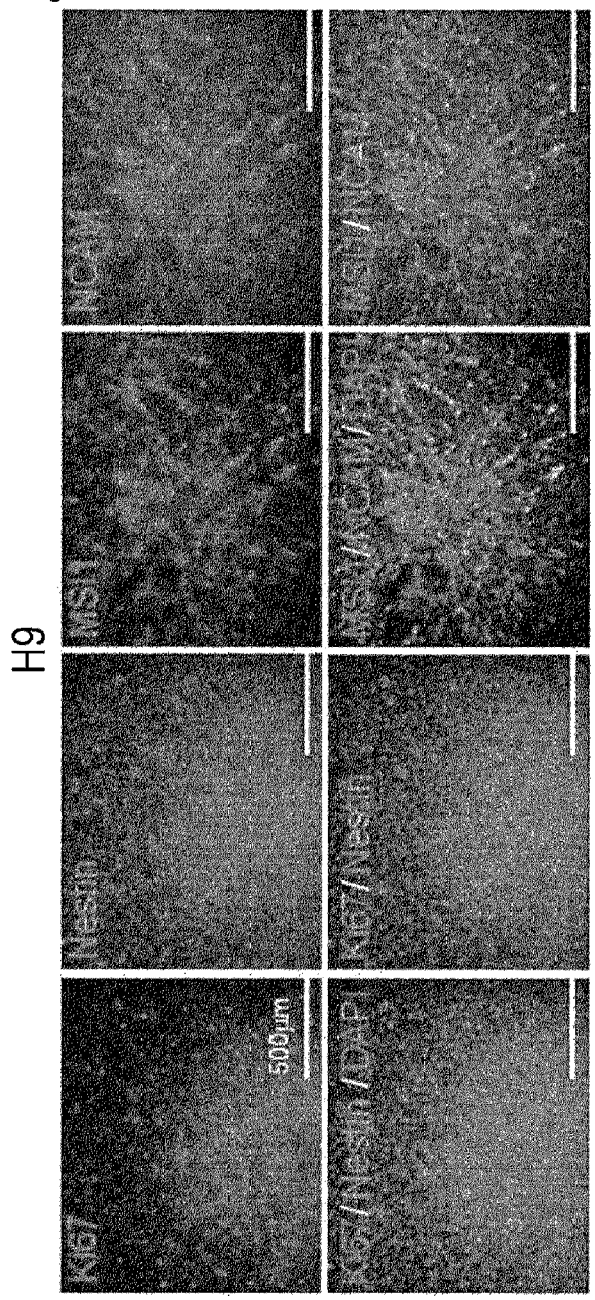
FIG. 9 shows a long-term culture of hESCs and hiPSCs in feeder-free NPY medium. Representative images of NESs stained either for Ki67 (cell proliferation marker), nestin, MSI1, and/or NCAM. Bar=500 μm.

In accordance with one preferred embodiment, two separately produced human embryonic stem cells (H9, HEUS-7) and human induced pluripotent stem cells were cultured under the culture conditions supplemented with various concentrations of NPY in the absence of conditioned medium or feeder cells for long-term undifferentiated growth of pluripotent stem cells. As a result, pluripotent stem cells can be maintained in an undifferentiated state in NPY medium (UM supplemented with 0.5 μM NPY) over 15 passages without feeder cells, which was confirmed by normal expression of hESC markers (FIG. 5), and retained normal karyotype (FIG. 6), capacity to differentiate into three germ layers in vitro by embryoid body formation (FIG. 7) and capacity of directed differentiation into a nervous system (FIGS. 8 and 9).

In addition, the maintenance of undifferentiated pluripotent stem cells can be confirmed by the increased expression of one or more genes selected from the group consisting of ALP (alkaline phosphatase), OCT-4, SOX2, hTERT (human telomerase reverse transcriptase), TDGF (teratocarcinoma-derived growth factor) and SSEA-4, but is not limited thereto.

Figure 5:
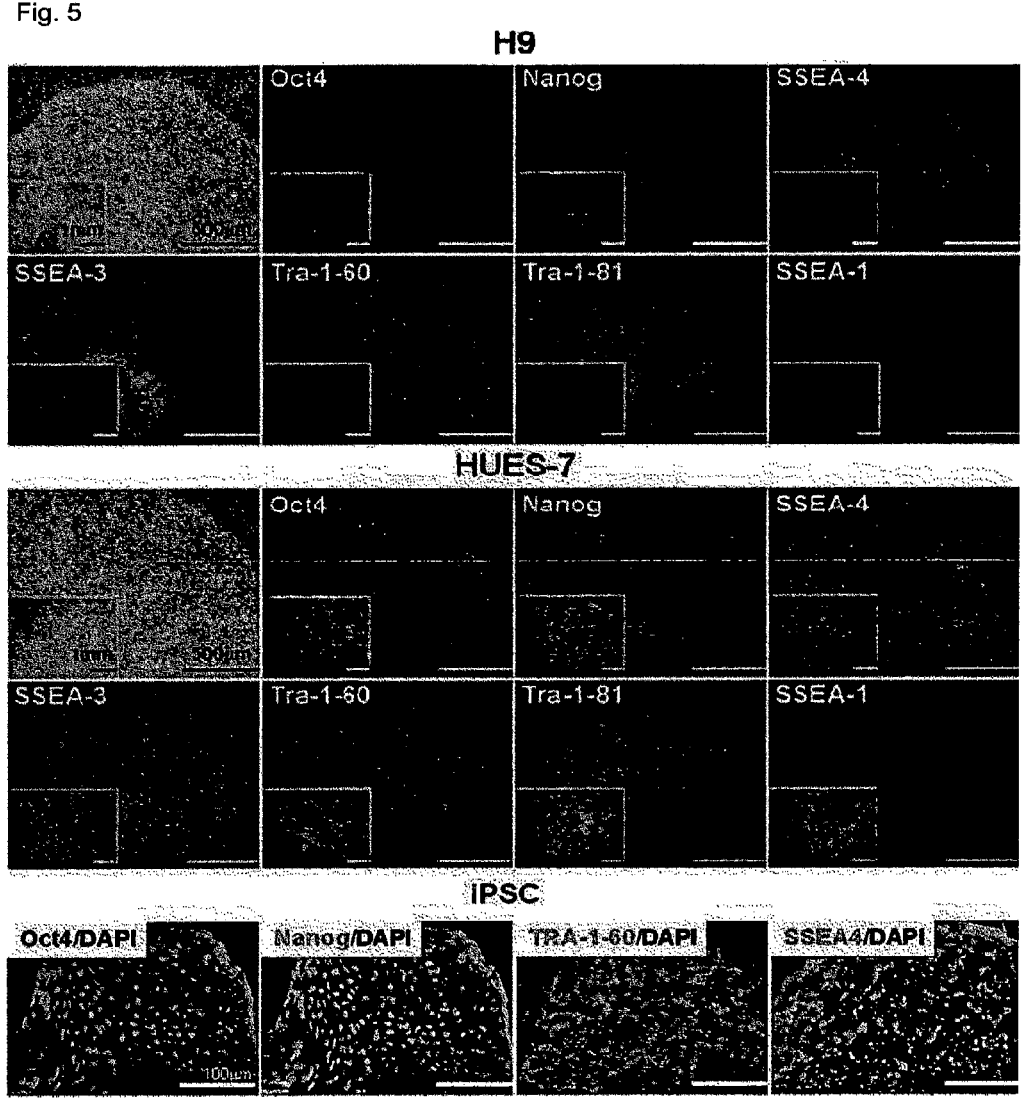
FIG. 5 shows a long-term culture of hESCs and hiPSCs in feeder-free NPY medium. Morphology of representative hESCs and hiPSCs colonies and immunohistochemical analysis of OCT4, NANOG, SSEA-4, SSEA-3, TRA-1-60 and TRA-1-80. H9 and HEUS-7 cells were cultured in NPY medium for 15 passages. Cellular nuclei were visualized by DAPI staining (insets). Bar=500 μm or 1 mm (inset images).

In accordance with one embodiment of the present invention, the maintenance of undifferentiated hESCs was confirmed by the positive expression of the hESC markers ALP, OCT-4, SOX2, hTERT, TEGF and SSEA-4 (FIGS. 2b and c). In addition, in order to confirm that pluripotent stem cells can be maintained in an undifferentiated state by addition of exogenous NPY without feeder cells for a long period time over 15 passages, expression levels of the hESC markers were examined (FIG. 5).

Further, the NPY-mediated maintenance and growth of undifferentiated pluripotent stem cells can be preferably mediated by activation of neuropeptide Y receptors, Y1 and Y5, and the activation of neuropeptide Y receptors, Y1 and Y5 can be achieved by activations of one or more signal pathways selected from AKT, ERK1/2, PKA, CREB and combinations thereof.

Figure 3:
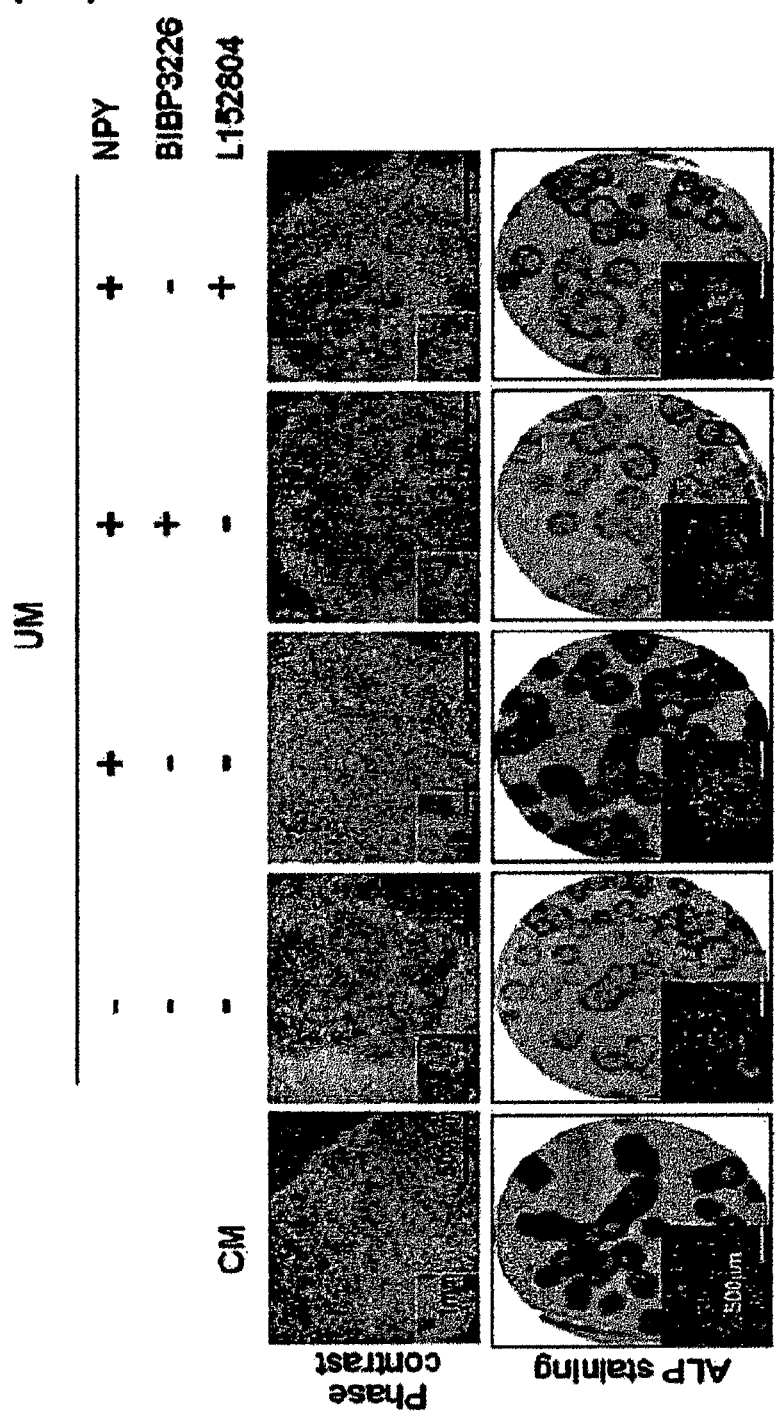
FIG. 3 shows the effect of selective NPY Y1 and Y5 receptor antagonists on hESC cultures. H9 hESCs were cultured for 5 days under feeder-free conditions using indicated media. (a) Representative phase contrast (upper panel) and ALP-stained images of H9 hESCs (lower panel) Bar=500 μm or 1 mm (inset images; upper panel). Scanned images of 35 mm round culture dishes and macroscopic images were acquired after ALP staining. Bar=500 μm (inset images; bottom panel). (b) Real-time qRT-PCR analysis for the expression of OCT4, SOX2, hTERT and TDGF. The results are displayed as the relative mRNA level with the level detected in undifferentiated hESCs cultured in MEF-CM set to 1 and are presented as the mean±SE (n=3).
Figure 14:
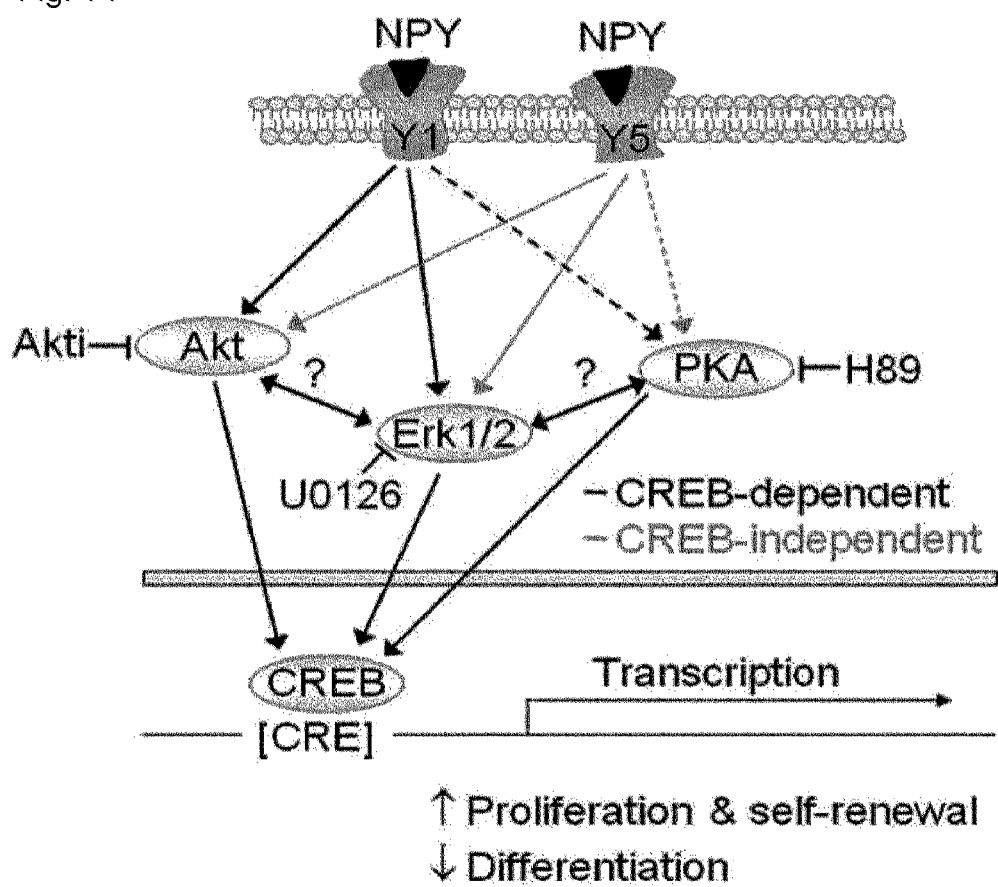
FIG. 14 shows the effect of NPY on intracellular signaling in hESCs. Simplified schematic of possible intracellular signaling pathways activated by NPY and the Y1 and Y5 receptors in hESCs.

In one embodiment of the present invention, it was further tested whether the effects of NPY on the undifferentiated maintenance and growth of human embryonic stem cells are associated with the signal pathway via the NPY receptors, Y1 and Y5. To examine NPY-specific NPY receptors that affect the undifferentiated maintenance of human embryonic stem cells, the selective Y1 and Y5 antagonists BIBP3226 (3 μM) and L152804 (3 μM) were used to inactivate Y1 and/or Y5, and then NPY-mediated maintenance of undifferentiated human embryonic stem cells were examined. As a result, loss of undifferentiated human embryonic stem cells was confirmed by morphological changes (FIG. 3a) and the diminished expression of undifferentiation-specific markers (FIGS. 3a and b). These results indicate that NPY-mediated maintenance of undifferentiated human embryonic stem cells is associated with NPY-mediated activation of Y1 and Y5 receptors. Further, it was confirmed that the loss of undifferentiated proliferation capacity of human embryonic stem cells by NPY stimulation is attributed to Y1 and/or Y5 antagonists (FIG. 4a) and AKT, ERK1/2 and PKA inhibitors (FIG. 4b). More specifically, to examine NPY-specific NPY receptors that contribute the undifferentiated proliferation of human embryonic stem cells, the selective Y1 and Y5 antagonists BIBP3226 (3 μM) and L152804 (3 μM) were used to inactivate Y1 and/or Y5, and then NPY-mediated growth rate of human embryonic stem cells was examined. As a result, the loss of undifferentiated proliferation capacity of human embryonic stem cells was confirmed by the lower number of BrdU+ cells (FIG. 4b). Therefore, these results indicate that NPY-mediated proliferation of undifferentiated human embryonic stem cells is associated with NPY-mediated activation of Y1 and Y5 receptors. Furthermore, in response to NPY, a transient increase in the level of phospho-AKT, phospho-ERK1/2 and phospho-CREB was observed (FIG. 10), NPY-mediated AKT, ERK1/2, and CREB phosphorylation was inhibited by Y1 and/or Y5 antagonists (FIG. 11), and NPY-mediated AKT, ERK1/2, and CREB phosphorylation was inhibited by each inhibitor of AKT, ERK1/2, and PKA (FIGS. 12 and d) (FIG. 14).

In still another aspect of the present invention, the present invention provides a dedifferentiation medium composition comprising neuropeptide Y (NPY).

Further, the present invention provides a method for inducing dedifferentiation, comprising the step of culturing differentiated cells in the dedifferentiation medium composition comprising neuropeptide Y.

Further, the present invention provides a method for establishing dedifferentiated cell lines, comprising the step of dedifferentiating differentiated cells under culture conditions including the above medium composition comprising neuropeptide Y.

Furthermore, the present invention provides an in vitro cell culture comprising differentiated cells, and the medium composition comprising neuropeptide Y, in which the differentiated cells are dedifferentiated.

As used herein, the term 'dedifferentiation', also referred to as a reprogramming process, means an epigenetic reverse process by which a terminally differentiated cell can be restored to an undifferentiated state where it has the potential to differentiate into a new cell type, and is based on reversibility of the epigenetic changes of the genome. In accordance with the object of the present invention, the 'dedifferentiation' includes any process by which differentiated cells having differentiation capacity of 0% to 100% are restored to an undifferentiated state, for example, the process may include a process by which differentiated cells having 0% differentiation capacity are dedifferentiated to cells having 1% differentiation capacity, and most preferably, a process by which differentiated cells having 0% differentiation capacity are dedifferentiated to cells having 100% differentiation capacity.

As used herein, the term 'dedifferentiated cell line' includes all cell lines produced by the above dedifferentiation process, and refers to a cell line having differentiation capacity of 0% to 100%. For example, a cell having 0% differentiation capacity is dedifferentiated to a cell having 1% differentiation capacity by the above dedifferentiation process, in which the cell having 1% differentiation capacity may be included in the dedifferentiated cell line. Examples of the dedifferentiated cell line may include progenitor cells and induced pluripotent stem cells, and most preferably induced pluripotent stem cells.

As used herein, the term 'differentiated cell' means a cell having differentiation capacity of 0% to 100%. Therefore, all cells, of which entire or parts can be undifferentiated by dedifferentiation, may be included in the differentiated cell and for example, somatic cells and progenitor cells may be included. The cells having 0% differentiation capacity may be somatic cells.

Preferably, the dedifferentiation medium composition of the present invention is able to dedifferentiate somatic cells or progenitor cells into induced pluripotent stem cells or dedifferentiate progenitor cells into induced pluripotent stem cells.

As used herein, the term 'somatic cells', cells constituting the adult body, mean cells having limited differentiation capacity and self-renewal capacity.

As used herein, the term 'progenitor cells' are cells that will differentiate into specialized cell types or to form specialized tissue prior to differentiation into cells of a given phenotype and function, and have self-renewal capacity but very restricted differentiation capacity. all of the endodermal, mesodermal and ectodermal progenitor cells are included.

In this connection, the dedifferentiation medium composition is able to dedifferentiate all or part of the differentiated cells into undifferentiated cells.

In this connection, the differentiated cells or/and dedifferentiated cell lines or/and induced pluripotent stem cells include differentiated cells or/and dedifferentiated cell line or/and induced pluripotent stem cells derived from any animal including humans, monkeys, pigs, horses, cows, sheep, dogs, cats, mice, rabbits, etc., with preference for humans.

In accordance with one specific embodiment of the present invention, the medium composition may contain neuropeptide Y in the range from 0.01 to 100 μM, and more preferably from 0.1 to 10 μM.

Figure 20:
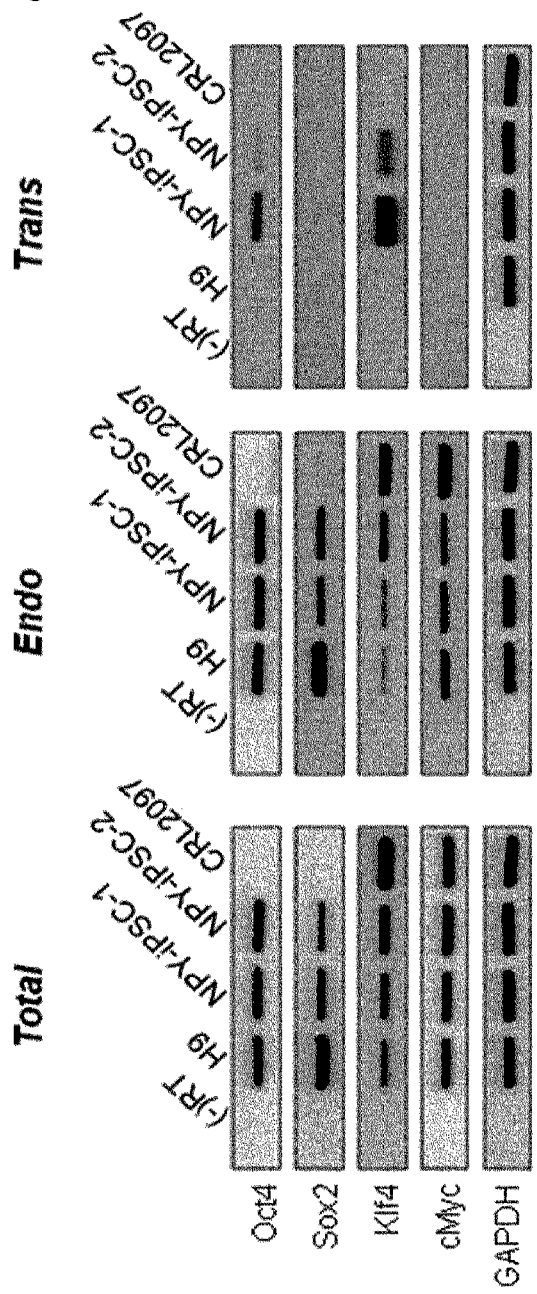
FIG. 20 shows the result of analyzing the properties of induced pluripotent stem cells produced under NPY culture conditions. RT-PCR analysis for the expression of hESC-specific markers in induced pluripotent stem cells produced under NPY culture conditions.
Figure 21:
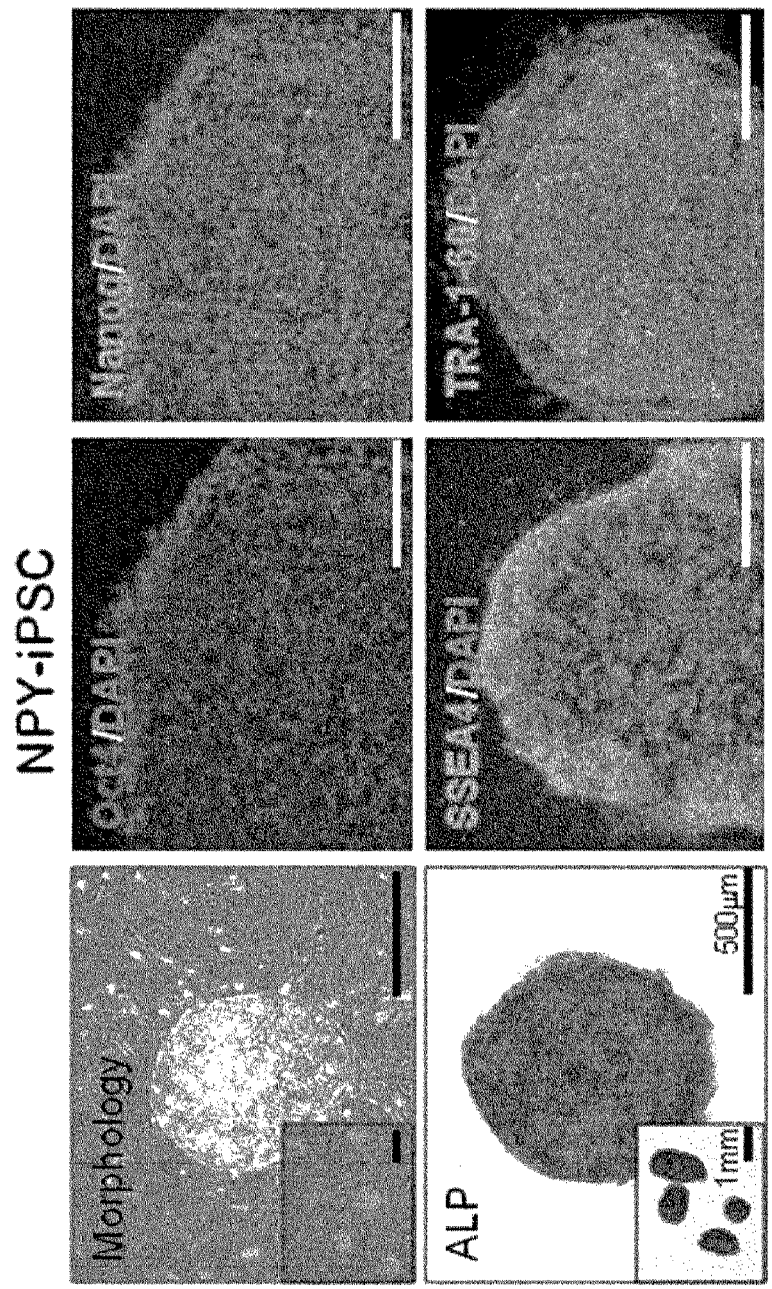
FIG. 21 shows the result of analyzing the properties of induced pluripotent stem cells produced under NPY culture conditions. Immunohistochemical analysis for the expression of hESC-specific markers in induced pluripotent stem cells produced under NPY culture conditions.
Figure 23:
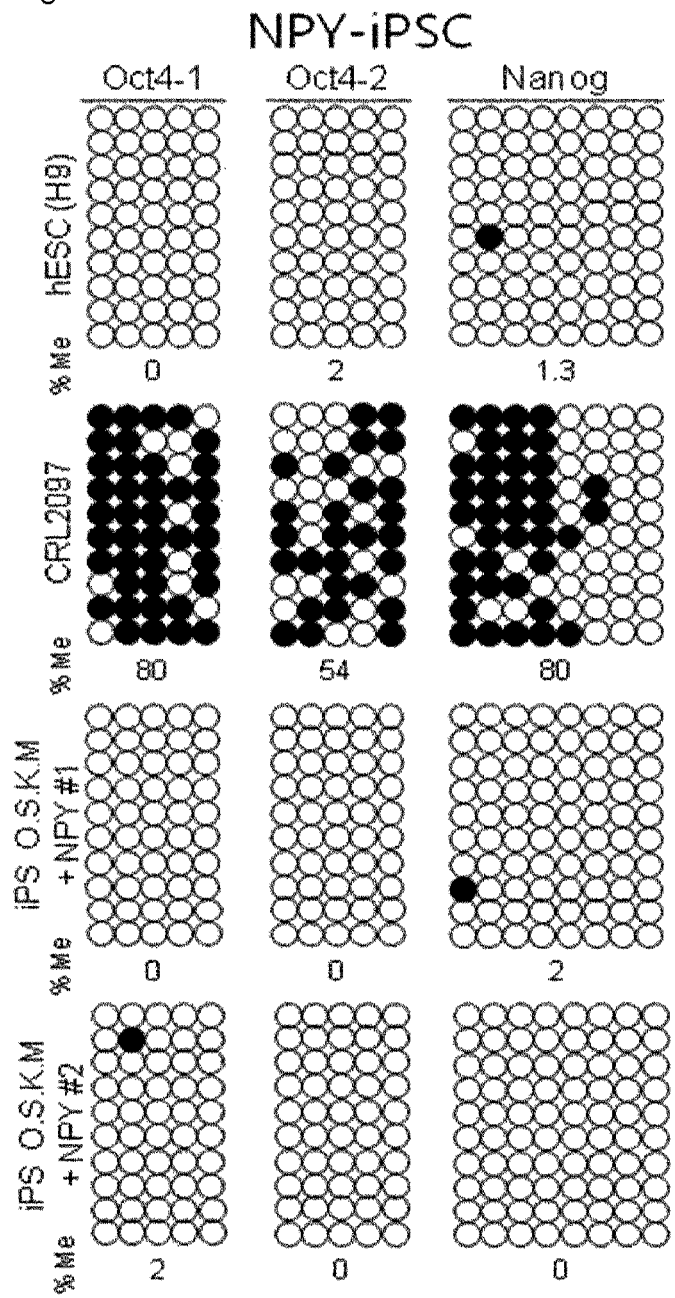
FIG. 23 shows the result of analyzing the properties of induced pluripotent stem cells produced under NPY culture conditions. Promoter methylation patterns of Oct3/4 and Nanog transcription factors in iPSCs produced under NPY supplemented culture conditions.
Figure 24:
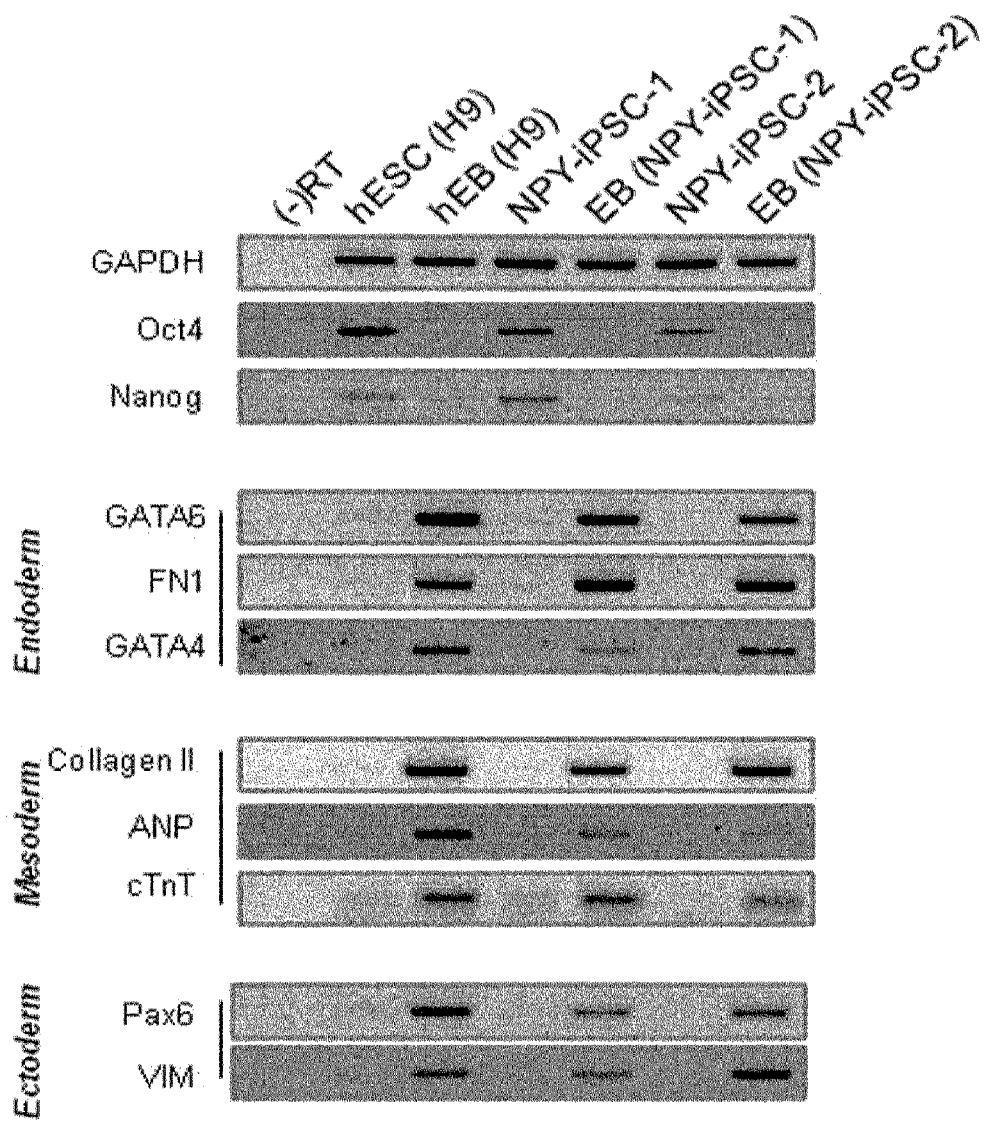
FIG. 24 shows the result of analyzing the properties of induced pluripotent stem cells produced under NPY culture conditions. Capacity to differentiate into three germ layers was evaluated by RT-PCR analysis for the expression of three germ layer-specific markers.
Figure 25:
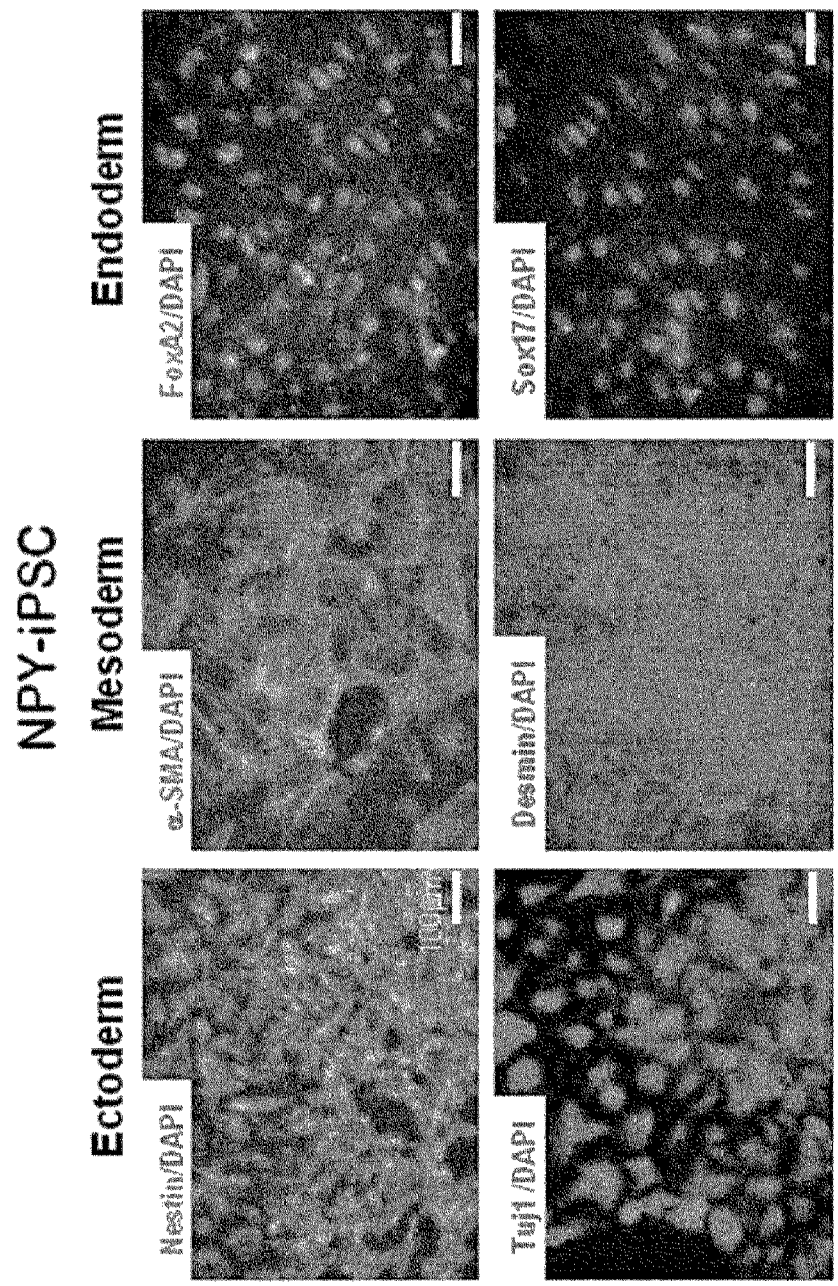
FIG. 25 shows the result of analyzing the properties of induced pluripotent stem cells produced under NPY culture conditions. Capacity to differentiate into three germ layers was evaluated by immunohistochemical analysis for the expression of three germ layer-specific markers.

In accordance with one specific embodiment of the present invention, dedifferentiation of induced pluripotent stem cells from human somatic cells was induced by retroviral transduction of the dedifferentiation factors, Oct4, Sox2, Klf4, and c-Myc in NPY (>0.1 μM) medium. As a result, compared to the control group without NPY, the dedifferentiation efficiency of yielding the induced pluripotent stem cell line was remarkably increased, as confirmed by an increase in the number of ALP positive colony (FIG. 19), and the induced pluripotent stem cells were found to have the differentiation capacity similar to embryonic stem cells, as confirmed by expression of hESC markers (FIGS. 20 and 21), insertion of reprogramming transcription factor into host genomic DNA (FIG. 22), CpG demethylation in the reprogramming transcription factors, OCT4 and NANOG promoters (FIG. 23), and differentiation capacity into three germ layers (FIGS. 24 and 25).

MODE FOR THE INVENTION

Hereinafter, the preferred Examples are provided for better understanding. However, these Examples are for illustrative purposes only, and the invention is not intended to be limited by these Examples.

Example 1

Human Pluripotent Stem Cell Culture

Two human embryonic stem cell lines H9 (NIH Code, WA09; WiCell Research Institute, Madison, Wis.) and HUES-7 (Harvard University, Cambridge, Mass.), and H1 (NIH Code, WA01; WiCell Research Institute) and the induced pluripotent stem cells were maintained according to a typical method of hESC culture (Kim MS (2007) Lab Chip 7, 513-515). For feeder-free culture, human embryonic stem cells and induced pluripotent stem cells were grown on plates coated with Matrigel (BD Biosciences, Franklin Lakes, N.J.) in MEF-conditioned medium (MEF-CM) or unconditioned medium (UM) with or without human NPY (Tyr-Pro-Ser-Lys-Pro-Asp-Asn-Pro-Gly-Glu-Asp-Ala-Pro-Ala-Glu-Asp-Leu-Ala-Arg-Tyr-Tyr-Ser-Ala-Leu-Arg-His-Tyr-Ile-Asn-Leu-Ile-Thr-Arg-Gln-Arg-Tyr-$NH_2$; SEQ ID No.1; Sigma). These cultured human embryonic stem cells were passaged once per week following collagenase IV (1 mg/ml; Invitrogen) or dispase (1 mg/ml; Invitrogen) treatment. The MEF-CM was prepared using v-irradiated MEFs as previously described (Xu C. Nat Biotechnol 19, 971-974), and the MEF-CM was supplemented with 8 ng/ml bFGF. UM contains 80% DMEM/F12, 20% KSR, 1% NEAA, 1 mM L-glutamine, 0.1 mM β-mercaptoethanol (Sigma) and 4 ng/ml bFGF. For feeder- and serum-free culture, human embryonic stem cells were grown in N2/B27-based medium containing DMEM/F12, 1×N2/B27 (Invitrogen), 1% NEAA, 1 mM L-glutamine, and 0.1 mM β-mercaptoethanol with or without NPY and TGFβ (R&D systems, Minneapolis, Minn.).

Example 2

Alkaline Phosphatase Staining

Staining for alkaline phosphatase (ALP) was performed using a commercially available ALP kit according to the manufacturer's instruction (Sigma). Images of ALP-positive cells were recorded by using a HP Scanjet G4010. The bright field images were also obtained using an Olympus microscope (IX51, Olympus, Japan).

Example 3

Flow Cytometry

Human embryonic stem cells were harvested and analyzed for the expression of SSEA-4 and ALP by flow cytometry.

Specifically, human embryonic stem cells were dissociated in cell dissociation buffer (Invitrogen), filtered through a 40 μm nylon cell strainer (BD Biosciences) and resuspended to approximately $5\times10^5$ cells in 100 μL PBS containing 0.1% BSA. Cells were incubated with primary antibodies including ALP (R&D systems, 1 μg/test) and SSEA-4 (R&D systems, 1 μg/test), diluted in PBS containing 0.1% BSA at 4° C. for 30 min. After washing, the cells were incubated with FITC-conjugated goat anti-mouse IgG (Santa Cruz Biotechnology, Santa Cruz, Calif.) for 30 min at 4° C. Cells were analyzed on FACSCalibur flow cytometer (Becton Dickinson, San Jose, Calif.) using CellQuest software. A total of 10,000 events were acquired, and the analysis was restricted to live events based on forward and side scatter. The percentage of positive cells was assessed after correction for the percentage of cells that stained with a FITC-conjugated isotype control antibody.

Example 4

Karyotype Analysis

Human embryonic stem cells cultured in UM supplemented with 0.5 μM NPY (NPY medium) for 15 passages were processed for G-banding. Representative images were taken using ChIPS-Karyo (Chromosome Image Processing System, GenDix).

Example 5

Embryoid Body Differentiation

To examine the potential of hESC differentiation, human embryoid bodies (hEBs) were prepared by culturing human embryonic stem cells in hEB culture medium (DMEM/F12 containing 10% SR (serum replacement)) in suspension using non-tissue culture-treated Petri dishes. After 5 days of growth in suspension, hEBs were transferred to gelatin-coated plates and attached to the bottom of the plates, where they were left to differentiate for an additional 15 days.

Example 6

BrdU Incorporation

Human embryonic stem cells were grown on matrigel-coated 4-well LabTec chamber slides for 4 days for the 5-bromo-2-deoxyuridine (BrdU; BD Pharmingen, San Diego) incorporation assays.

For BrdU incorporation, the cells were incubated in the presence of 30 μM BrdU for 1 hr at 37° C. After washing with PBS, the cells were fixed with 4% paraformaldehyde for 15 min, and incubated in 1 N HCl for 15 min at room temperature. The samples were then washed and incubated with 0.1 M sodium tetraborate for 15 min. After washing, the cells were incubated with the anti-BrdU antibody in PBS supplemented with 3% BSA for 1 hr, and then incubated with a FITC-conjugated secondary antibody (Invitrogen) for 30 min. The nuclei were stained with DAPI and examined using an Olympus microscope. The mean number of BrdU+ cells per field of vision was determined. At least four fields of vision per coverslip were counted.

Example 7

Growth Efficiency Test hESC clumps (100×100 μm; approximately 70-90 cells per clump) was seeded evenly on a 35 mm culture dish coated with Matrigel in a final volume of 2 ml. The cells were plated to a cell density of approximately $5 \times 10^5$ cells per 35 mm culture dish. The plated cells were allowed to grow for 6 days under described culture conditions. To determine the number of cells, the cells were washed with PBS and trypsinized. The cell suspension was mixed with a 0.4% (wt/vol) trypan blue solution, and the number of live cells was determined using a hemocytometer. Each trial was performed in triplicate.

Example 8

RT-PCR and Quantitative Real-Time PCR

Total RNA was extracted from human embryonic stem cells using an RNeasy Mini Kit (Qiagen, Valencia, Calif.). cDNA synthesis was performed by using a SuperScript First-strand Synthesis System kit (Invitrogen). RT-PCR was performed using a platinum PCR SuperMix kit (Invitrogen) under the following conditions: 3 min at 94° C., and then 28 cycles of 30 sec at 94° C., 30 sec at 60° C., and 30 sec at 72° C., followed by 10 min 72° C. extension after the cycles. Real-time qPCR was performed using QuantiTect SYBR Green PCR Master Mix (Qiagen) on the 7500 Real-Time PCR System (Applied Biosystems, Foster City, Calif.) under the following conditions: 10 min at 95° C.; 40 cycles of 15 sec at 95° C. and 1 min at 60° C. Each experiment was carried out at least three times. The expression value of each gene was normalized to the amount of GAPDH transcript to calculate a relative amount of mRNA present in each sample. Error bars represent standard error of the mean (n=3). The Primers used are listed in Table 1.

TABLE 1

List of primers used

| Gene | Primer (Forward) | SEQ ID NO. | Primer (Reverse) | SEQ ID NO. | Accession No. |
|---|---|---|---|---|---|
| GAPDH | GAAGGTGAAGGTCGGAGTC | 2 | GAAGATGGTGATGGGATTTC | 3 | NM_002046 |
| OCT4 | GAGAAGGATGTGGTCCGAGTGTG | 4 | CAGAGGAAAGGACACTGGTCCC | 5 | NM_002701 |
| SOX2 | AGAACCCCAAGATGCACAAC | 6 | ATGTAGGTCTGCGAGCTGGT | 7 | NM_024865 |
| hTERT | CGGAAGAGTGTCTGGAGCAA | 8 | GGATGAAGCGGAGTCTGGA | 9 | NM_198255.1 |
| TDGF | TCCTTCTACGGACGGAACTG | 10 | AGAAATGCCTGAGGAAAGCA | 11 | NM_003212.1 |
| hNPY | TGCTAGGTAACAAGCGACTG | 12 | CTGCATGCATTGGTAGGATG | 13 | NM_000905 |
| hNPYJR | ACCACTGGGTCTTTGGTGAG | 14 | AAGGCAAAGAAGAAGCCACA | 15 | NM_000909 |
| hNPYR5 | GGGTCCCCACTTGCTTTGAGATA | 16 | GTTCTTTCCTTGGTAAACAGTGAG | 17 | NM_006174 |
| mNPY | TGGACTGACCCTCGCTCTAT | 18 | TCACCACATGGAAGGGTCTT | 19 | NM_023456 |
| mNPY1R | GTCCTTGCAGTGGCTTCTTC | 20 | TGATTCGCTTGGTCTCACTG | 21 | NM_010934 |
| mNPY2R | GAGGTGCAGGTGATCCTCAT | 22 | TTTCCACTCTCCCATCAAGG | 23 | NM_008731 |
| mNPYR5 | TGTGGATTGTCCCACAAAGA | 24 | CATCCAGCTAACAGCGAACA | 25 | NM_016708 |
| Sox1 | GGGAAAACGGGCAAAATAAT | 26 | CCATCTGGGCTTCAAGTGTT | 27 | NM_005986 |
| Pax6 | ATGAGGCTCAAATGCGACTT | 28 | CATTTGGCCCTTCGATTAGA | 29 | NM_001604 |
| MsII | TTCGGGTTTGTCACGTTTGAG | 30 | GGCCTGTATAACTCCGGCTG | 31 | NM_002442 |
| Nestin | AACAGCGACGGAGGTCTCTA | 32 | TTCTCTTGTCCCGCAGACTT | 33 | NM_006617 |

TABLE 1-continued

List of primers used

| Gene | Primer (Forward) | SEQ ID NO. | Primer (Reverse) | SEQ ID NO. | Accession No. |
|---|---|---|---|---|---|
| Sox3 | GACGCCTTGTTTAGCTTTGC | 34 | TTCTCCCATTCACTCCTTGG | 35 | NM_005634 |
| MAP2 | GACATGCAAGGCACAGAAGA | 36 | TTTTCCCTCATGGGAGTCAG | 37 | NM_002374 |

Example 9

Immunocytochemistry

For immunostaining, cells were plated on matrigel-coated 4-well Lab-Tek chamber slides (Nunc, Naperville, Ill.) and cultured for 5 days under described conditions. The Cells were fixed in 4% paraformaldehyde for 15 min at room temperature (RT). After washing, with PBS/0.2% BSA, cells were permeabilized in PBS/0.2% BSA/0.1% Triton X-100 for 15 min and blocked in 4% normal donkey serum (Molecular Probes, Eugene, Oreg., USA) in PBS/0.2% BSA for 1 hr at room temperature. Cells were incubated for 2 hrs at 4° C. with respective primary antibodies diluted in PBS/0.2% BSA. After washing, cells were incubated with FITC- or Alexa 594-conjugated secondary antibodies (Invitrogen) in PBS/0.2% BSA for 1 hr at room temperature. Cells were counterstained using 10 µg/ml DAPI (4',6-diamidino-2-phenylindole). Chamber slides were analyzed by an Olympus microscope or Axiovert 200M microscope (Carl Zeiss, Gottingen, Germany). Antibodies used are listed in Table 2.

min, and protein concentrations determined using the BCA protein assay kit (Pierce, Rockford, Ill.). Proteins (20 µg) were fractionated by SDS polyacrylamide gel electrophoresis (PAGE), and electrotransferred to polyvinylidene fluoride (PVDF) membranes (Millipore Corp, Bedford, Mass.). Membranes were blocked in PBS containing 0.1% Tween-20 and 5% non-fat milk for 2 hrs at room temperature, and probed with primary antibodies diluted in PBS/0.2% BSA for 1 hr. After washing, membranes were incubation with the corresponding secondary anti-rabbit HRP-conjugated or anti-mouse HRP-conjugated antibodies (Amersham, Arlington Heights, Ill.), and the bands were visualized using the ECL Advance kit (Amersham). Bands were analyzed for density with Image Gauge software (Fuji Photo Film GMBH, D) and normalized to loading control (β-actin) bands. All experiments were performed in triplicate. Error bars represent standard error of the mean (n=3). Antibodies used are listed in Table 2.

TABLE 2

List of Antibodies used

| Antibodies | Catalog No. | Company | Dihition |
|---|---|---|---|
| anti-NPY | sc-133080 | Santa Cruz Biotechnology | 1:50 for immunostaining |
| anti-Oct4 | sc-9081 | Santa Cruz Biotechnology | 1:50 for immunostaining |
| anti-Nanog | sc-33759 | Santa Cruz Biotechnology | 1:200 for immunostaining |
| anti-SSEA-3 | MAB1434 | R&D Systems | 1:50 for immunostaining |
| anti-SSEA-4 | MAB1435 | R&D Systems | 1:50 for immunostaining |
| anti-TRA-1-60 | MAB4360 | Chemicon | 1:100 for immunostaining |
| anti-TRA-1-81 | MAB4381 | Chemicon | 1:100 for immunostaining |
| anti-SSEA-1 | MAB2155 | R&D Systems | 1:50 for immunostaining |
| anti-phospho-CREB | 9198 | Cell Signaling | 1:50 for immunostaining |
| anti-nestin | MAB5326 | Chemicon | 1:200 for immunostaining |
| anti-PAX6 | | DSHB at the University of Iowa | 1:50 for immunostaining |
| anti-MSI1 | AB5977 | Chemicon | 1:100 for immunostaining |
| anti-NCAM | MAB5324 | Chemicon | 1:200 for immunostaining |
| anti-Ki67 | NCL-Ki67p | Novocastra Laboratories | 1:200 for immunostaining |
| anti-phospho-Akt (Ser$^{473}$) | 9271 | Cell Signaling | 1:1000 for western blotting |
| anti-Akt | 9272 | Cell Signaling | 1:1000 for western blotting |
| anti-phospho-Erk1/2 (Thr$^{202}$/Tyr$^{204}$) | 9101 | Cell Signaling | 1:1000 for western blotting |
| anti-Erk1/2 | sc-93 | Santa Cruz biotechnology | 1:1000 for western blotting |
| anti-phospho-CREB (Ser$^{133}$) | 9191 | Cell Signaling | 1:1000 for western blotting |
| anti-CREB | 9197 | Cell Signaling | 1:1000 for western blotting |
| anti-β-actin | A1978 | Sigma | 1:5000 for western blotting |

Example 10

Western Blot Analysis

Human embryonic stem cells were lysed in RIPA buffer containing 50 mM Tris, pH 8.0, 150 mM NaCl, 1% NP-40, 0.1% SDS, 0.5% deoxycholic acid, 1 mM PMSF, and a cocktail of protease inhibitors (Roche Applied Science, Indianapolis, Ind.) for 15 min on ice and centrifuged at 20,000×g for 10 min at 4° C. The supernatant was re-centrifuged for 10

Example 11

Derivation of Neuroectodermal Spheres from hESCs

To generate hEBs, small-sized hESC clumps were transferred into non-tissue culture-treated Petri dishes and cultured in hEB culture medium for 7 days. To derivate neuroectodermal spheres (NESs), hEBs were cultured in a NES culture medium (MEM/F12 supplemented in 1×N2/B27 (Invitrogen), 20 ng/ml epidermal growth factor (Invitrogen), 20 ng/ml bFGF, 10 ng/ml leukemia inhibitory factor (Sigma) and 100 U/ml penicillin-streptomycin). At this stage, the cells were defined as passage 1 (PI). The culture medium was refreshed every 2 days, and the NESs were sub-cultured every week using a McIlwain tissue chopper (Mickle Engineering, Gomshall, Surrey, UK).

Example 12

Production of Dedifferentiation Factor-Expressing Retrovirus

For virus production, each retroviral vector for the dedifferentiation transcription factors Oct4, Sox2, Klf4, and cMyc was transfected into HEK 293 cells (GP2 293) with Gag/pol using lipofectamine 2000 (Invitrogen). Four complexes of dedifferentiation factor-inserted vector-lipofectamine 2000 were formed, respectively and 500 ul of the solution was added to the cells cultured in media, followed by gentle mixing and cultivation for 16 hrs. To examine transfection efficiency, a pMXs-EGFP-Rheb-IP vector was used. Next day, the media was replaced with fresh media, and after 24 hrs, supernatant was taken and filtered using a 0.45 um (Millipore) filter to remove cell debris. GFP positive cells were observed under a fluorescence microscope to examine the transfection efficiency. The filtered supernatant was centrifuged at 20,000 rpm for 2 hrs to remove supernatant, and the remaining pellet was concentrated in HBSS (Cibco). To confirm the efficiency, the virus solution obtained by transfection of pMXs-EGFP-Rheb-IP vector was used, and virus titers, namely, MOT values were determined by FACS analysis and fluorescence microscopy. Specifically, each of serially diluted virus concentrates was transduced into somatic cells, and the next day, the media was replaced with fresh media. After 5 days, trypsin treatment was performed for single-cell dissociation. Propidium iodide (PI) was added to PBS supplemented with 1% BSA, and 10,000 cells were analyzed using a FACScalibur (BD bioscience). The number of GFP positive cells was counted to determine MOI values.

Example 13

Production of Induced Pluripotent Stem Cells

Virus concentrations at an MOI of 1~5 and 6-8 µg/ml polybrene (sigma) were added to somatic fibroblasts, and after 24 hr cultivation, the media was replaced with fresh media. After 5-day cultivation, Trypsin-EDTA was used to detach the cells, and then the cells were added to feeder cells, and cultured in somatic cell medium. Next day, the media was replaced with hESC medium, and after approximately 2 weeks, cells showing typical hESC morphology were produced, and the cells were passaged. During the dedifferentiation process, various concentrations of NPY (0.1-10 mM) were added to the somatic cell medium and hESC medium, and its effect on dedifferentiation efficiency was confirmed by changes in cell morphology and expression of hESC markers.

Example 14

Analysis on Promoter Methylation of Reprogramming Transcription Factors

To examine properties of the induced pluripotent stem cells produced by using human embryonic stem cells and Oct4, Sox2, or cMyc gene-inserted retrovirus, promoter methylation patterns of hESC-specific transcription factors, Oct3/4 and Nanog were analyzed. To extract genomic DNA, human embryonic stem cells and induced pluripotent stem cells cultured in hESC media for 6 days were extracted using a DNA extraction kit (Qiagen Genomic DNA purification kit). Bisulfite sequencing was performed by three steps: step 1 is to treat DNA with sodium bisulfite ($NaHSO_3$), step 2 is to perform PCR of the region of interest (promoter region), and step 3 is to analyze DNA methylation patterns by sequencing of the PCR product. DNA treatment with sodium bisulfite was performed using a commercially available EZ DNA Methylation Kit (Zymo Research). When DNA is treated with bisulfite, methylated cytosine remains unmodified, whereas non-methylated cytosine is converted into uracil. Thus, when PCR is performed using each of primers specific to cytosine and uracil base sequences, methylated and non-methylated DNA can be distinguished from each other. Base sequences of the primers are shown in Table 3. A PCR reaction mixture was prepared to a final volume of 20 µL, containing 1 µg of bisulfite-treated DNA, 0.25 mM/L deoxynucleoside triphosphates, 1.5 mM/L $MgCl_2$, 50 µM primer, 1 PCR buffer, 2.5 units of Taq polymerase (Platinum Taq DNA polymerase, Invitrogen, Carlsbad, Calif., USA). In addition, the PCR reactions were performed under the following conditions: 10 min at 95° C., and 40 cycles of 1 min at 95° C., 1 min at 60° C., and 1 min at 72° C., and then 10 min at 72° C. The PCR products were analyzed in a 1.5% agarose gel, and after gel elution, cloned into a pCR2.1-TOPO vector (Invitrogen). The methylated and non-methylated base sequences were sequenced using M13 forward and M13 reverse primers.

TABLE 3

| Gene | Primer (Forward) | Primer (Reverse) | Accession No. |
|---|---|---|---|
| For bisulfate sequencing | | | |
| bi Oct4-3 | ATTTGTTTTTTGGGTAGTTAA AGGT (SEQ ID No. 38) | CCAACTATCTTCATCT TAATAACATCC (SEQ ID No. 39) | NM_002701 |
| bi Oct4-4 | GGATGTTATTAAGATGAAGAT AGTTGG (SEQ ID No. 40) | CCTAAACTCCCCTTCA AAATCTATT (SEQ ID No. 41) | NM_002701 |
| bi Nanog | TGGTTAGGTTGGTTTTAAATT TTTG (SEQ ID No. 42) | AACCCACCCTTATAAA TTCTCAATTA (SEQ ID No. 43) | NM_024865 |

Result

1. Human Embryonic Stem Cells, Human Induced Pluripotent Stem Cells and MEFS Express NPY and NPY Receptors RT-PCR analysis was performed to examine expression of NPY and NPY receptors in undifferentiated human embryonic stem cells (H9, HUES-7, H1). As a result, expression of the NPY, NPY Y1 and NPY Y5 transcripts were primarily detected, while the mRNAs encoding Y2 and Y4 were not detected (FIG. 1a), which is consistent with a meta-analysis of 38 different array experiments (Assou S, et al. (2007) A meta-analysis of human pluripotent stem cells transcriptome integrated into a web-based expression atlas. Stem Cells 25, 961-973) (the world wide web at amazonia.montp.inserm.fr/). Similarly, in human induced pluripotent stem cells, the expression of the NPY, NPY Y1 and NPY Y5 transcripts were detected, while the mRNAs encoding Y2 and Y4 were not detected (FIG. 1a). In MEF feeders, the expression of the mRNAs encoding NPY, Y1, Y2 and Y5 were detected, while the mRNA encoding Y4 was not detected (FIG. 1a). A sequence analysis confirmed that the sequence of the RT-PCR products was 100% identical to the published human NPY, NPY Y1 and NPY Y5 receptor sequences (data not shown). The expression of the mature NPY proteins in undifferentiated human embryonic stem cells and MEFs was further evaluated by immunocytochemical analysis. The NPY proteins were found in both the nuclei and cytoplasm of undifferentiated human embryonic stem cells and MEFs (FIG. 1b). To test whether the expression of NPY and its receptors are influenced by the differentiation status of the human embryonic stem cells, the relative mRNA expression level of NPY and its receptors were compared between undifferentiated human embryonic stem cells, retinoic acid (RA)-differentiated human embryonic stem cells, and differentiating human embryoid bodies using qRT-PCR. The differentiation of the human embryonic stem cells was confirmed by the down-regulation of the hESC-specific markers OCT4 and NANOG (FIG. 1c). The mRNA expression of NPY, Y1 and Y5 was altered upon human embryonic stem cell differentiation. Compared to undifferentiated human embryonic stem cells, the expression of both the NPY and Y1 mRNAs was down-regulated in RA-differentiated human embryonic stem cells, but their expression was increased in differentiating human embryoid bodies. The present inventors also observed that the expression of Y5 receptor was down-regulated both in RA-differentiated human embryonic stem cells and differentiating human embryoid bodies to a different extent (FIG. 1c). Similar results were obtained from two independent human embryonic stem cell lines. These results indicate that changes in the level of NPY and/or its receptor may be associated with the different differentiation stages of human embryonic stem cells.

2. Exogenous NPY Supports the Maintenance of Undifferentiated Human Embryonic Stem Cells and Human Induced Pluripotent Stem Cells, and the Selective Inhibition of Y1 and Y5 Induces Loss of Undifferentiation Capacity and Self-Renewal Capacity of Human Embryonic Stem Cells To examine NPY functions on self-renewal capacity of human embryonic stem cells and human induced pluripotent stem cells, the present inventors cultured human embryonic stem cells and human induced pluripotent stem cells on plates coated with Matrigel under feeder-free conditions using MEF-conditioned medium (MEF-CM) or unconditioned medium (UM) with various concentrations of NPY, and monitored the changes in the morphology and the expression of hESC specific markers. The human embryonic stem cells and human induced pluripotent stem cells cultured in unconditioned medium (UM) for 5 days (FIG. 2a) lost their undifferentiated state and underwent the early phases of differentiation, as indicated by morphological changes and the down-regulation of hESC markers. In contrast, human embryonic stem cells and human induced pluripotent stem cells cultured in UM plus NPY (>0.1 µM) significantly maintained their undifferentiated state after one and two consecutive passages, as characterized by the typical hESC morphology (FIG. 2a) and the positive expression of the hESC markers. The addition of 0.5 µM NPY to UM effectively supported the maintenance of undifferentiated human embryonic stem cells (FIGS. 2a and 2c) and human induced pluripotent stem cells (FIG. 2a), almost to a similar extent as human embryonic stem cells cultured in MEF-CM (CM-hESCs) or UM plus high amounts of bFGF (=40 ng/ml) (FIGS. 2a and 2c). The present inventors further tested whether of the effects of NPY on the maintenance of human embryonic stem cells are mediated through the Y1 and/or Y5 using selective Y1 (BIBP3226) and Y5 antagonists (L152804). In the presence of either BIBP3226 (3 µM) or L152804 (3 µM), human embryonic stem cells cultured in NPY medium fail to maintain in an undifferentiated state and underwent differentiation within 4 days, as confirmed by morphological changes (FIG. 3a) and the diminished expression of hESC markers, ALP, OCT4, SOX2, hTERT and TDGF (FIGS. 3a and b).

These results indicate that the NPY signal pathway via Y1 and Y5 receptors plays an important role in undifferentiated maintenance of human embryonic stem cells, and blocking of the signal pathway induces loss of hESC self-renewal capacity.

Figure 4:
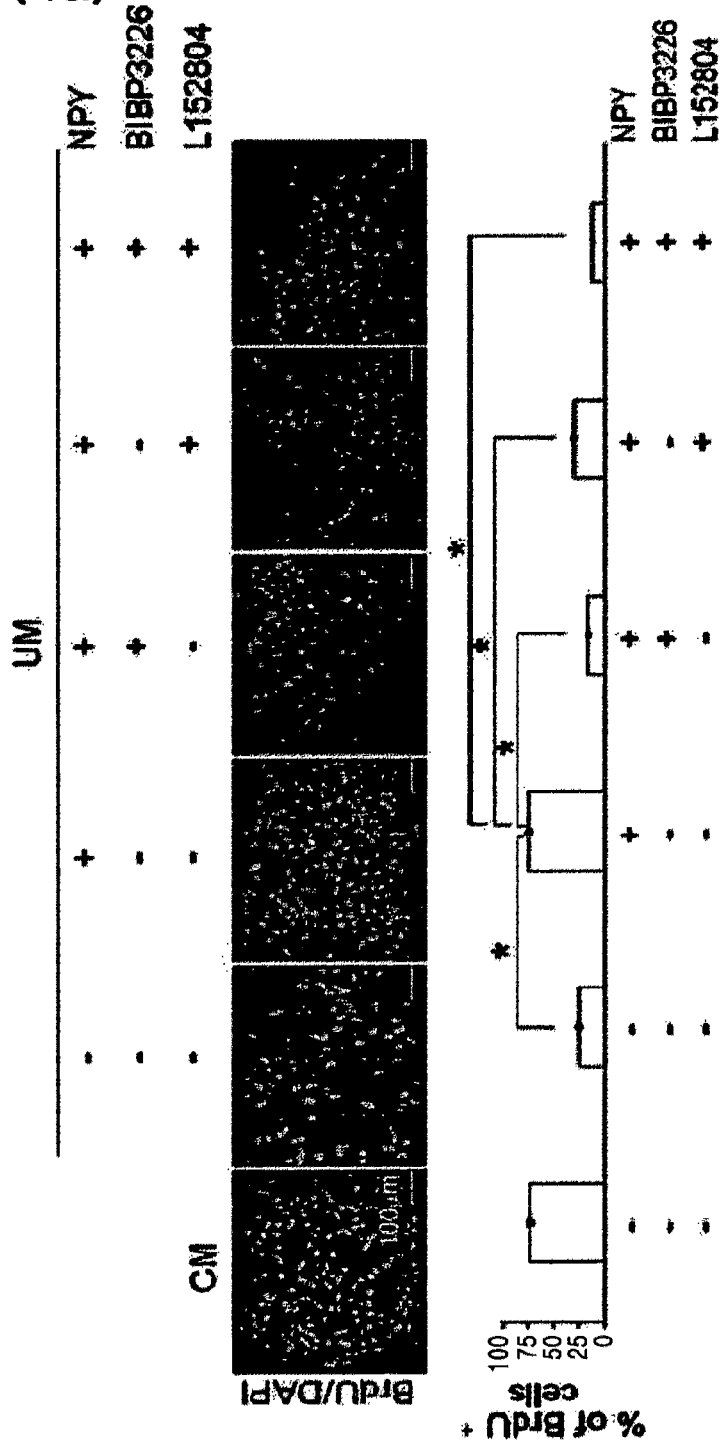
FIG. 4 shows the effect of NPY on hESC proliferation. The proliferation rate of H9 hESCs cultured using the indicated media was measured using BrdU incorporation. NPY-mediated hESC proliferation was measured in the presence or absence of NPY Y1 (BIBP3226; 3 μM) and Y5 (L152804; 3 μM) receptor antagonists (a) and AKT (AKTi; 10 μM), ERK1/2 (U0126; 10 μM) or PKA (H89; 10 μM) inhibitor (b). Upper panels: representative images of BrdU+ cells. Bar=100 μm. Lower panels: Quantification of BrdU+ cells. The relative number of BrdU+ cells per field of vision was quantified and is presented as the percentage of the total number of cells counted. The data is presented as the mean±SE (n=3). *p<0.01, by t-test.

3. Proliferation of Undifferentiated Human Embryonic Stem Cells Maintained in NPY Medium To better understand the role of NPY on human embryonic stem cells, the present inventors tested the direct effect of NPY on proliferation of human embryonic stem cells by assessing BrdU incorporation. Human embryonic stem cells cultured in UM, which lost their undifferentiated state, displayed a lower rate of BrdU incorporation (24.5±2.3%) when compared with undifferentiated human embryonic stem cells cultured in MEF-CM (72.4±2.9%; FIG. 4). The addition of 0.5 µM NPY to the UM resulted in a significant increase in the BrdU incorporation by the human embryonic stem cells, reaching levels comparable to human embryonic stem cells cultured in MEF-CM (FIG. 4a). No significant difference was seen in the number of BrdU+ cells between human embryonic stem cells (72.4±2.9%; FIG. 4a) cultured in NPY medium (73.4±2.9%) and human embryonic stem cells cultured in MEF-CM (72.4±2.9%; FIG. 4a).

To further evaluate the contribution of Y1 and Y5 in NPY-mediated proliferation of pluripotent stem cells, the present inventors added the selective antagonists BIBP3226 or L152804 to NPY medium, and cultured human embryonic stem cells to count the number of BrdU+ cells. The number of BrdU+ cells was significantly lower in NPY medium with 3 µM BIBP3226 (16.3±1.7%) or 3 µM L152804 (29.1±1.8%) than in NPY medium alone (73.4±2.9%; FIG. 4a). The addition of Y1 and Y5 antagonists together had an additive effect on the suppression of proliferation of human embryonic stem cells (11.7±0.6%). These results indicate that the use of NPY in the culture of human embryonic stem cells without feeder cell-derived factors effectively maintains undifferentiated proliferation of human embryonic stem cells, and the effect of NPY on the proliferation of human embryonic stem cells appears to be mediated by the activation of both the Y1 and Y5 receptors.

The present inventors further explored whether PI3K/AKT, MAPK/ERK1/2 and PKA signaling is involved in mediating the proliferative effect of NPY on pluripotent stem cells using the selective inhibitors of the respective signaling cascades. As shown in FIG. 4b, the inhibitors of Akt (AKTi), ERK1/2 (U0126) and PKA (H89) were, potent in suppressing NPY-stimulated BrdU incorporation. These results suggest that the proliferative effect of NPY on human embryonic stem cells is mediated through the Y1 and Y5 receptors that trigger multiple intracellular signaling pathways including AKT, ERK1/2 and PKA.

4. Exogenous NPY can be Used as a Medium Composition for Long-Term, Feeder-Free Culture of Undifferentiated Human Embryonic Stem Cells The present inventors evaluated whether NPY substantially improves the culture conditions without feeder cell-derived factors. The long-term, continuous culture of two different human embryonic stem cells lines were maintained in an undifferentiated state in NPY medium (UM supplemented with 0.5 µM NPY) for more than 15 passages over months, as confirmed by the normal expression of hESC markers (FIG. 5). Similarly, the normal expression of hESC markers was also observed in human induced pluripotent stem cells cultured in NPY medium (FIG. 5). Human embryonic stem cells cultured in NPY medium (NPY-hESCs) showed a normal karyotype (FIG. 6) and had the same growth rate during the cultivation period as those cultured in MEF-CM (FIG. 4a). To confirm pluripotency of the human embryonic stem cells cultured in NPY medium for 15 passages, human embryoid bodies (hEBs) were formed in suspension for 5 days, and transferred to gelatin-coated dishes and cultured for 15 additional days for further differentiation (FIG. 7). Real-time RT-PCR demonstrated that a marked reduction in the expression of the hESC marker OCT-4 was observed and the markers specific for ectoderm (PAX6, NCAM), mesoderms (GATA2, cTnT), and endoderm (GATA6, α-FP) were highly expressed in embryoid bodies from human embryonic stem cells cultured in NPY medium, which was similar to human embryoid bodies from human embryonic stem cells cultured in CM (FIG. 7). These results indicate that the human embryonic stem cells maintained in NPY medium retain the potential to form derivatives of all three embryonic germ layers and are pluripotent.

The present inventors further tested whether directed differentiation of human pluripotent stem cells cultured in NPY medium into the neuroectodermal lineage could be induced. Human embryoid bodies from human embryonic stem cells cultured in NPY medium were continuously cultivated in neuroectodermal sphere (NES)-culture medium. After 7-10 days of incubation, they displayed a rosette structure (FIG. 8). Their neural identity was confirmed by the expression of neural precursor markers, such as SOX1, PAX6, MSI1, NES, SOX3 and MAP2, using semi-quantitative RT-PCR (FIG. 8). The majority of the differentiating cells expressed the proliferation marker ki67 and the neural precursor markers, NES, MSI1 and NCAM (FIG. 9). These results indicate that human embryonic stem cells cultured in NPY medium can be successfully differentiated into neural cells and are pluripotent.

Figure 10:
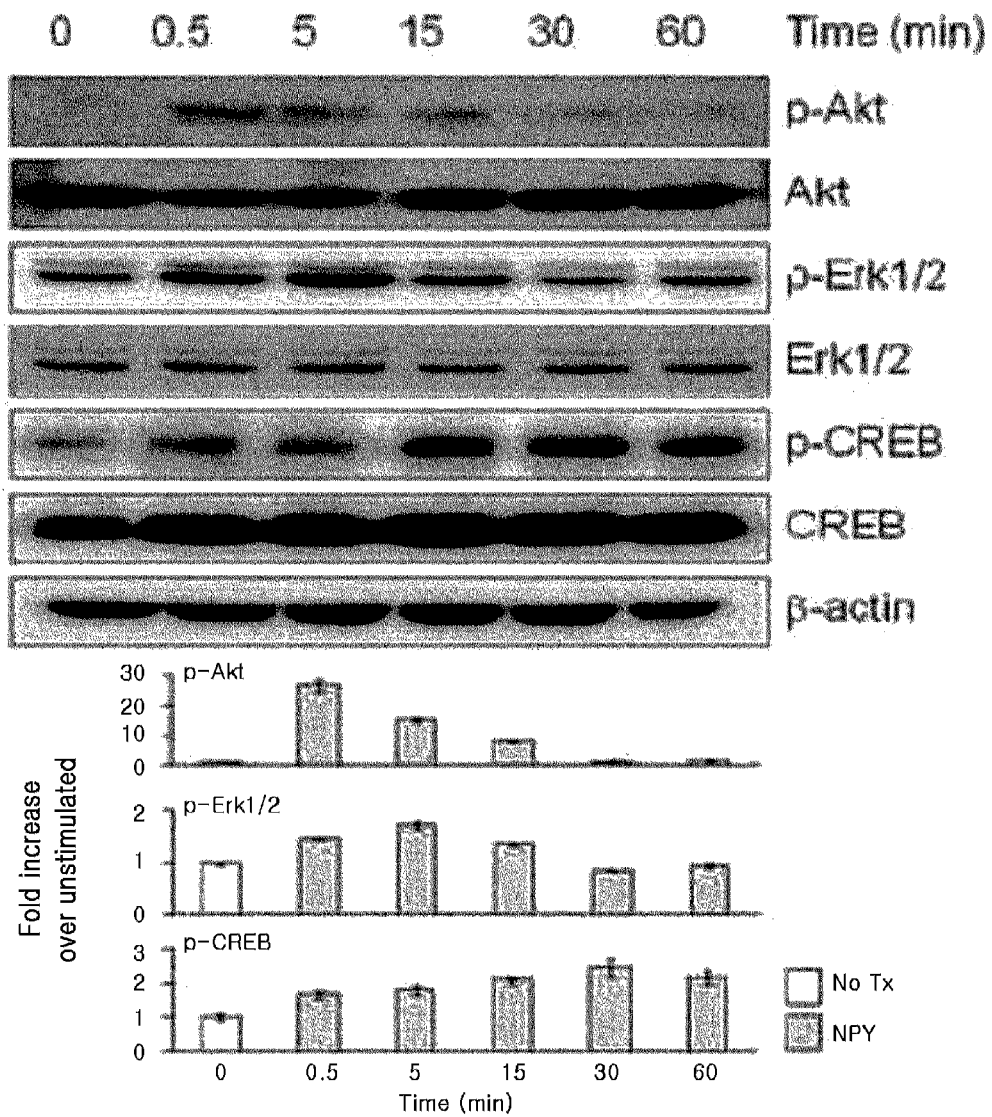
FIG. 10 shows the effect of NPY on intracellular signaling in hESCs. Western blot of H9 cells treated with 1 μM NPY for the indicated times.
Figure 11:
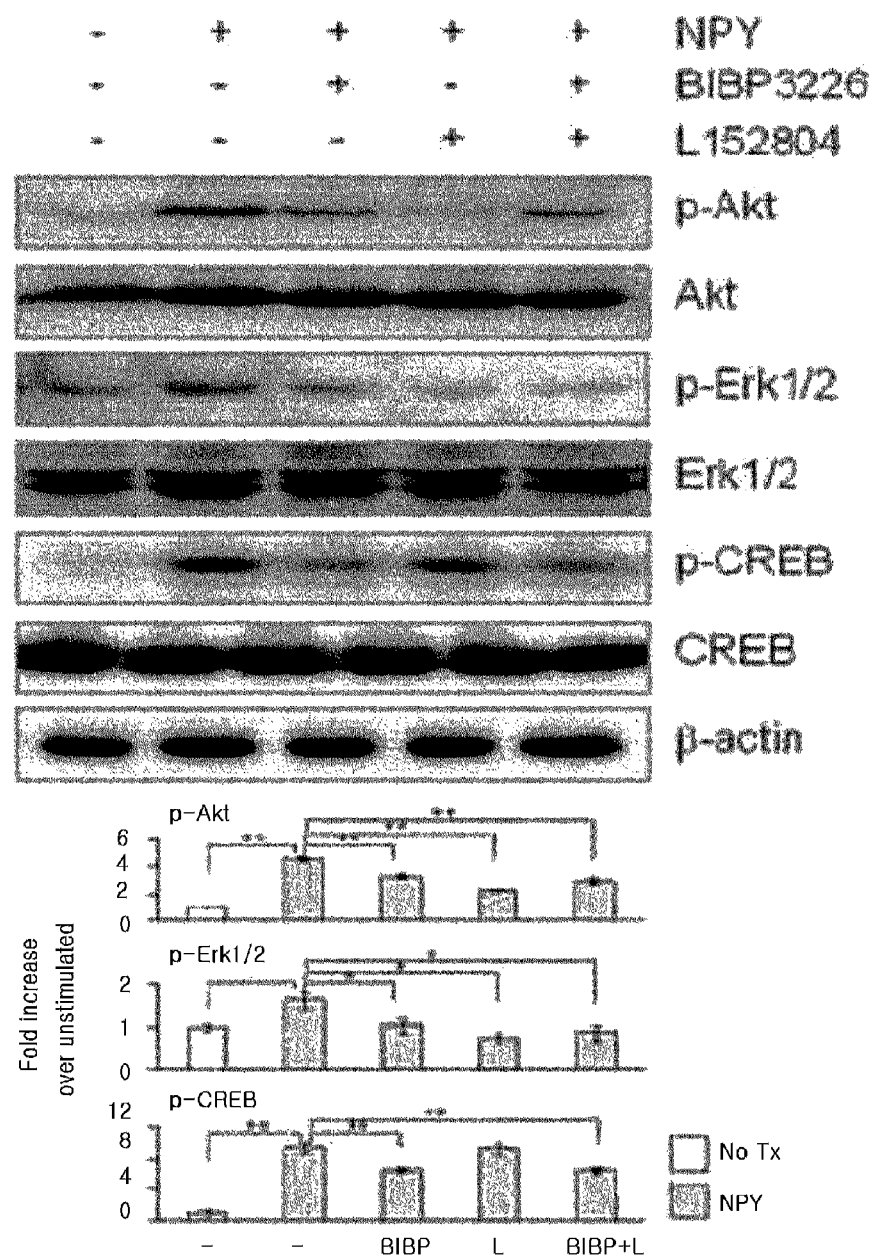
FIG. 11 shows the effect of NPY on intracellular signaling in hESCs. Western blot of H9 cells treated with 1 μM NPY for 5 min with or without a 1 hr pretreatment with 3 μM BIBP3226 (BIBP) or 3 μM L-152804 (L).
Figure 12:
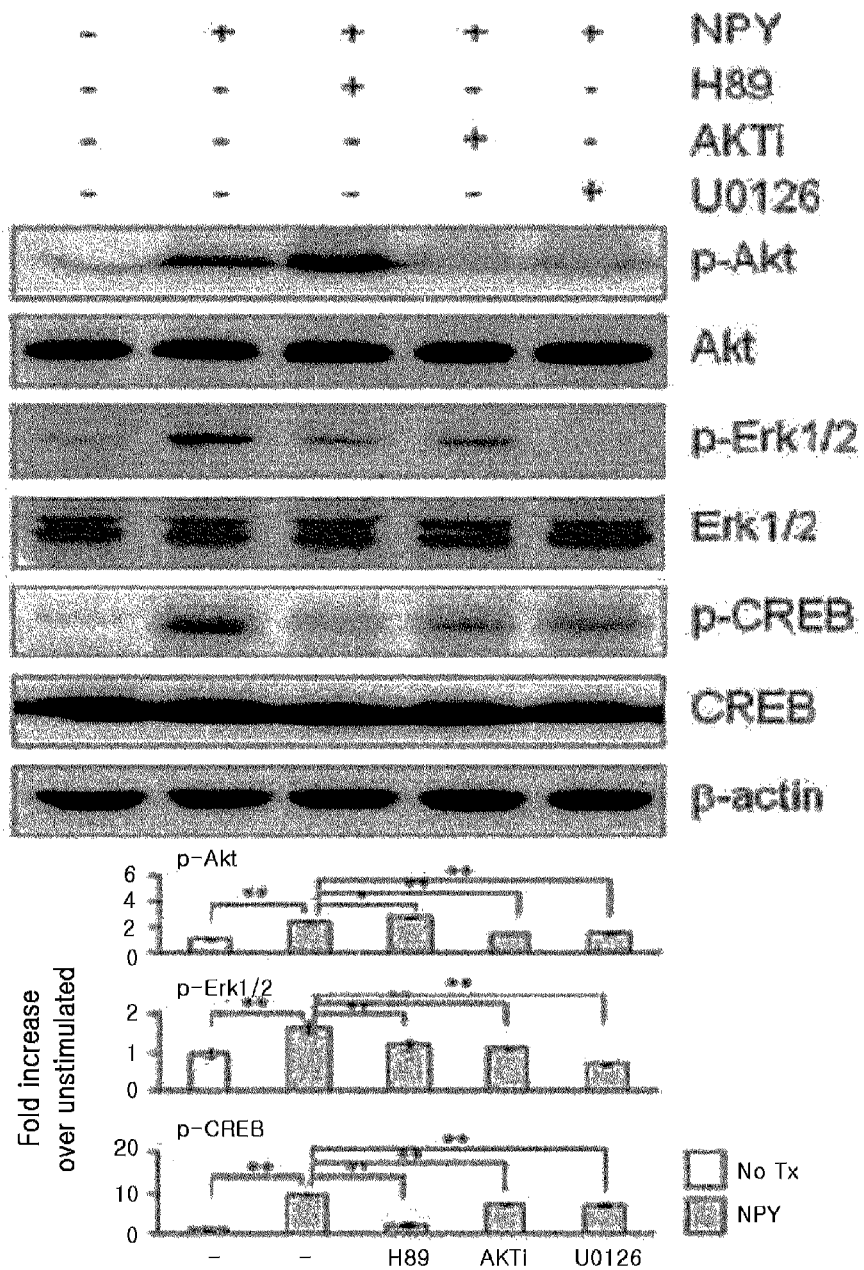
FIG. 12 shows the effect of NPY on intracellular signaling in hESCs. Western blot of H9 cells treated with 1 μM NPY for 5 min with or without a 1 hr pretreatment with 10 μM AKTi, 10 μM U0126 or 10 μM H89. The membranes were probed with the indicated antibodies, and β-actin was used as a loading control. For protein quantification, the blots were scanned, and the bands were quantified using densitometry (a-c, lower panels). The data are presented as the mean±SE (n=3). **p<0.01, *p<0.05, by t-test.

5. NPY Activates Multiple Pathways Including Akt, ERK1/2, PKA, and CREB in hESCs To analyze the effect of NPY-mediated pathway in human pluripotent stem cells, the present inventors evaluated the activation of AKT, ERK1/2, PKA and CREB signal transduction cascades. In response to NPY, a transient increase in the level of phospho-AKT (pAKT) and phospho-ERK (pERK) in human embryonic stem cells was observed within 1 min, while the total expression of AKT and ERK was not changed (FIG. 10). The phosphorylation of AKT peaked 0.5 min after the application of 1 µM NPY and this activation decreased to the basal level by 60 min. The phosphorylation of ERK1/2 peaked 5 min after the addition of NPY and dropped to the basal level by 30 min (FIG. 10). In contrast, both the total and phosphorylated p38 and JNK protein levels remained stable following NPY addition (data not shown). NPY-mediated AKT and ERK activation was significantly reduced by a 30 min pretreatment with an Y1 or Y5 receptor antagonist. However, co-treatment with the Y1 and Y5 antagonists showed no additive or synergistic effects (FIG. 11). The NPY-mediated AKT activation was inhibited by pretreatment of with an AKT or ERK1/2 inhibitor, but not with a PKA inhibitor. In contrast, the NPY-mediated ERK activation was blocked by all three inhibitors (FIG. 12).

Figure 13:
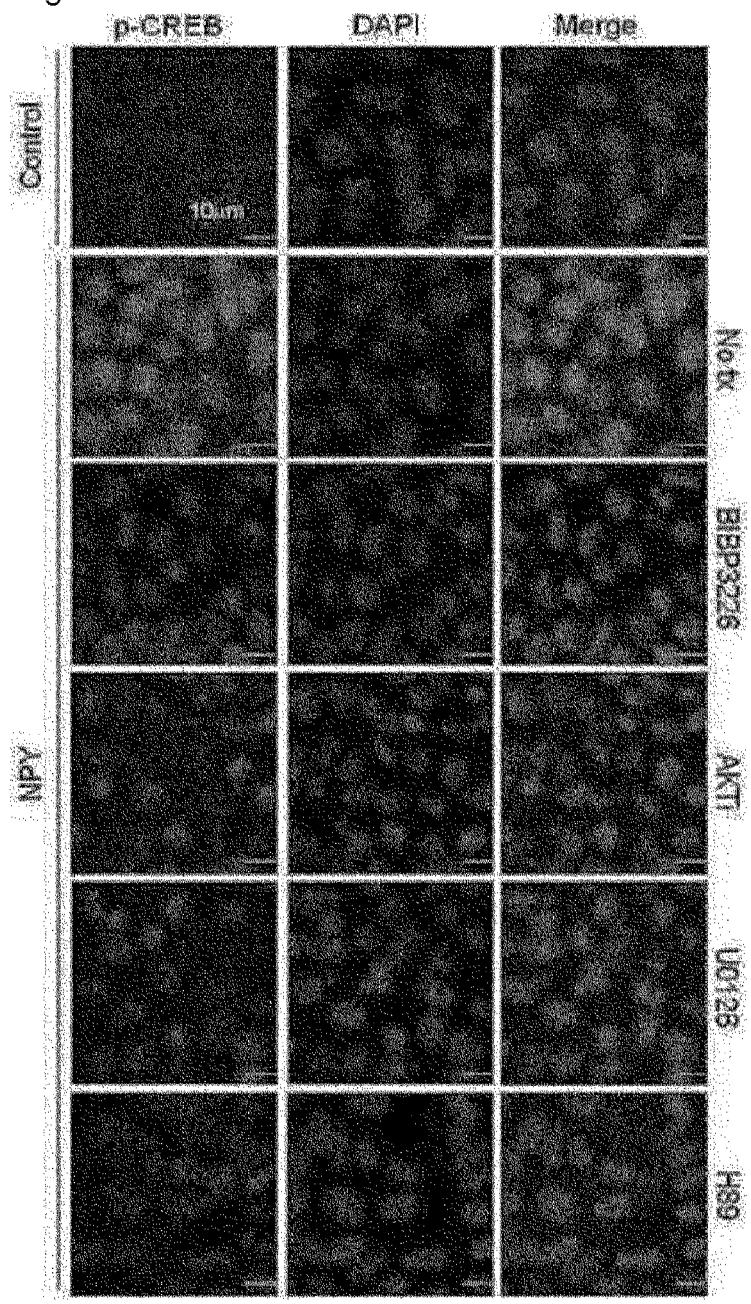
FIG. 13 shows the effect of NPY on intracellular signaling in hESCs. Immunohistochemical analysis of hESCs treated with 1 μM NPY for 5 min with or without a 1 hr pretreatment with 3 μM BIBP3226, 10 μM AKTi, 10 μM U0126 or 10 μM H89.

The present inventors further investigated whether CREB signaling is involved in the NPY-mediated signal transduction by determining the expression level of CREB and phospho-CREB (p-CREB). In response to 1 µM of NPY, human embryonic stem cells exhibited a rapid increase of p-CREB in min without a significant change in the total CREB protein level (FIG. 10). The p-CREB was predominantly localized to the nucleus in NPY-treated human embryonic stem cells (FIG. 13). The pretreatment with the Y1 antagonist, but not the Y5 antagonist, partially blocked the NPY-mediated up-regulation of p-CREB (FIGS. 11 and 14). Furthermore, pretreatment of human embryonic stem cells with inhibitors specific for AKT, ERK1/2 or PKA blocked the NPY-mediated CREB phosphorylation; however their ability to inhibit CREB phosphorylation appeared to be incomplete (FIG. 12). These data suggest that NPY-mediated CREB activation is mediated through AKT, ERK1/2 and PKA. The results indicate that NPY mediates its effects through the Y1 and Y5 receptors in human embryonic stem cells and that these effects are tightly associated with the concerted activation of the AKT, ERK1/2, PKA and CREB pathways. The cross-talk between these signaling pathways may be important in the NPY-mediated maintenance of undifferentiated human embryonic stem cells.

6. exogenous NPY can be Effectively Used to Improve the Culture Conditions without Feeder Cell-Derived Factors and Animal Serum To establish culture conditions using defined media free of feeder cell-derived factors and animal serum, the N2/B27 supplement and bFGF have been used together with NPY. Human embryonic stem cells cultured in N2/B27-based medium containing 20 ng/ml bFGF (N2/B27 medium) failed to maintain an undifferentiated state, proliferated less and differentiated to a greater extent. However, the addition of 1 µM NPY to N2/B27 medium containing 20 ng/ml of bFGF clearly minimized the spontaneous differentiation of human embryonic stem cells. Under such conditions, human embryonic stem cells retained their undifferentiated state for more than six passages, appeared similar way to human embryonic stem cells cultured in MEF-CM in terms of cell morphology, maintained normal hESC marker expression (FIG. 15) and retained a normal karyotype (FIG. 16). The addition of 1 mM NPY to N2/B27-based medium or UM clearly maintained the undifferentiated cell morphology, and growth efficiency and expression of the hESC markers in human embryonic stem cells appeared similar to the way undifferentiated human embryonic stem cells cultured in CM or with free-cells (FIG. 7).

The optimum and minimum concentration of NPY required for hESC culture was largely dependent upon the medium composition (0.5 µM in UM; 1 µM in N2/B27 medium), but its effect on the self-renewal capacity of human embryonic stem cells was dose dependent. A low concentration of TGFβ which is an important factor for hESC self-renewal, was used as a limiting component in hESC culture medium. In the present invention, long-term maintenance of undifferentiated human embryonic stem cells in vitro (≥15 passages) can be achieved by the addition of 1 ng/ml TGFβ to a defined N2/B27 medium containing 1 μM NPY. As compared with the hESC culture conditions using MEF-CM and UM supplemented with NPY, TGFβ addition did not affect the growth efficiency of human embryonic stem cells by measuring the cell number (FIGS. 17 and 18). The results suggest that the addition of NPY can effectively support undifferentiated maintenance of human embryonic stem cells in chemically defined medium without feeder cell-derived factors and animal serum.

Figure 19:
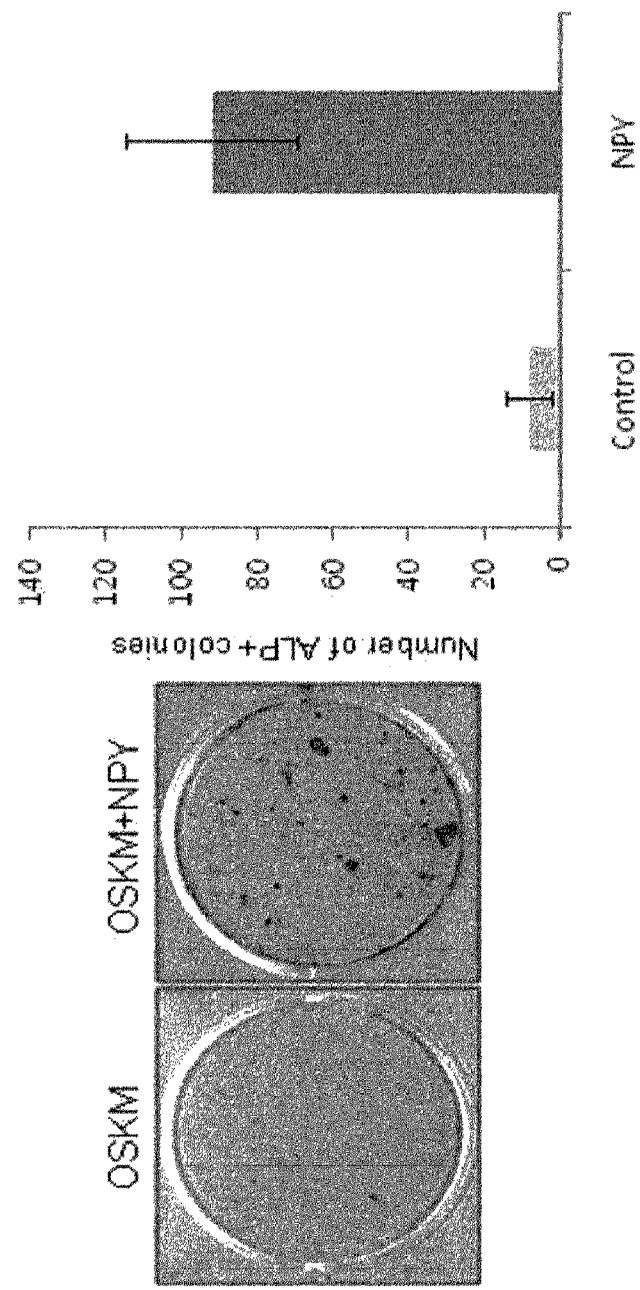
FIG. 19 shows the result of analyzing the properties of induced pluripotent stem cells produced under NPY culture conditions. Changes in dedifferentiation efficiency were evaluated in the presence or absence of NPY during the dedifferentiation process, based on cell morphology and ALP staining.
Figure 22:
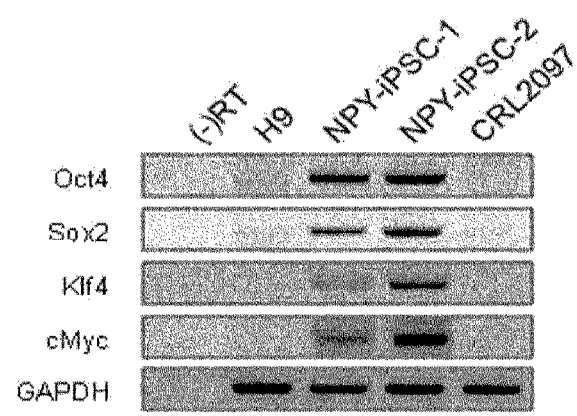
FIG. 22 shows the result of analyzing the properties of induced pluripotent stem cells produced under NPY culture conditions. Expression patterns of Oct3/4, Sox2, Klf4, and c-Myc transcription factors in host genomic DNA of iPSCs produced under NPY supplemented culture conditions.

7. Exogenous NPY Increases Dedifferentiation Efficiency During Production of Human Induced Pluripotent Stem Cells To examine the promoting effect of exogenous NPY during a reprogramming process of human somatic cells, a human somatic fibroblast cell line (ATCC, CRL-2097) was treated with Oct4 (O), Sox2 (S), Klf4 (K), or c-Myc (M)-inserted retrovirus solution, and various concentrations of NPY were added to the culture media. Production of induced pluripotent stem cells was observed by morphological analysis and ALP activity analysis. It was confirmed that dedifferentiation efficiency was increased under the NPY-added dedifferentiation culture conditions (more than 10 times), as compared to the non-treated control group (FIG. 19). Properties of induced pluripotent stem cells established under the NPY-added culture conditions were analyzed. As a result, it was confirmed that the expression of hESC-specific markers appeared similar to the way those in human embryonic stem cells at gene (FIG. 20) and protein (FIG. 21) levels, and exogenous reprogramming transcription factors were integrated within host genomic DNA (FIG. 22). Further, demethylation of Oct4 and Nanog promoter regions was observed in the induced pluripotent stem cells established under the NPY-added culture conditions (FIG. 23). Furthermore, their capacity to differentiate into three germ layers was confirmed by three germ layers-specific makers at the gene (FIG. 24) and protein (FIG. 25) levels.

The invention claimed is:

1. A method for maintaining undifferentiated human pluripotent stem cells, comprising culturing human pluripotent stem cells in a culture medium comprising neuropeptide Y whereby the undifferentiated pluripotent stem cells are maintained.

2. The method according to claim 1, wherein the pluripotent stem cells are embryonic stem cells or induced pluripotent stem cells.

3. The method according to claim 1, wherein the maintenance of the undifferentiated pluripotent stem cells is confirmed by the increased expression of one or more genes selected from the group consisting of ALP (alkaline phosphatase), OCT4, SOX2, hTERT (human telomerase reverse transcriptase), TDGF (teratocarcinoma-derived growth factor) and SSEA-4 as compared to the level of expression of the one or more genes in pluripotent cells cultured in the absence of neuropeptide Y.

4. The method according to claim 1, wherein the concentration of the neuropeptide Y is in the range of 0.01 to 100 μM.

5. The method according to claim 1, wherein the culture medium further comprises one or more factors selected from the group consisting of N2 supplement, B27 supplement, bFGF and TGFβ without animal serum and feeder cell-derived factors.

6. The method according to claim 5, wherein the N2 and B27 supplements are provided in a ratio of 1:1, and bFGF and TGFβ are provided at a concentration of 4-100 ng/ml and 1-10 ng/ml, respectively.

7. An in vitro cell culture comprising undifferentiated human pluripotent stem cells cultured according to the method of claim 1.

8. The in vitro cell culture according to claim 7, wherein the pluripotent stem cells are embryonic stem cells or induced pluripotent stem cells.

\* \* \* \* \*

SEQUENCE LISTING

<160> NUMBER OF SEQ ID NOS: 43

<210> SEQ ID NO 1
<211> LENGTH: 36
<212> TYPE: PRT
<213> ORGANISM: Homo sapiens

<400> SEQUENCE: 1

Tyr Pro Ser Lys Pro Asp Asn Pro Gly Glu Asp Ala Pro Ala Glu Asp
 1               5                  10                  15

Leu Ala Arg Tyr Tyr Ser Ala Leu Arg His Tyr Ile Asn Leu Ile Thr
            20                  25                  30

Arg Gln Arg Tyr
        35

<210> SEQ ID NO 2
<211> LENGTH: 19
<212> TYPE: DNA
<213> ORGANISM: Artificial Sequence
<220> FEATURE:
<223> OTHER INFORMATION: Forward Primer for GAPDH

<400> SEQUENCE: 2
gaaggtgaag gtcggagtc                                                19

<210> SEQ ID NO 3
<211> LENGTH: 20
<212> TYPE: DNA
<213> ORGANISM: Artificial Sequence
<220> FEATURE:
<223> OTHER INFORMATION: Reverse Primer for GAPDH

<400> SEQUENCE: 3
gaagatggtg atgggatttc                                               20

<210> SEQ ID NO 4
<211> LENGTH: 23
<212> TYPE: DNA
<213> ORGANISM: Artificial Sequence
<220> FEATURE:
<223> OTHER INFORMATION: Forward Primer for Oct4

<400> SEQUENCE: 4
gagaaggatg tggtccgagt gtg                                           23

<210> SEQ ID NO 5
<211> LENGTH: 22
<212> TYPE: DNA
<213> ORGANISM: Artificial Sequence
<220> FEATURE:
<223> OTHER INFORMATION: Reverse Primer for Oct4

<400> SEQUENCE: 5
cagaggaaag gacactggtc cc                                            22

<210> SEQ ID NO 6
<211> LENGTH: 20
<212> TYPE: DNA
<213> ORGANISM: Artificial Sequence
<220> FEATURE:
<223> OTHER INFORMATION: Forward Primer for SOX2

<400> SEQUENCE: 6
agaaccccaa gatgcacaac                                               20

<210> SEQ ID NO 7
<211> LENGTH: 20
<212> TYPE: DNA
<213> ORGANISM: Artificial Sequence
<220> FEATURE:
<223> OTHER INFORMATION: Reverse Primer for SOX2

<400> SEQUENCE: 7
atgtaggtct gcgagctggt                                               20

<210> SEQ ID NO 8
<211> LENGTH: 20
<212> TYPE: DNA
<213> ORGANISM: Artificial Sequence
<220> FEATURE:
<223> OTHER INFORMATION: Forward Primer for hTERT

<400> SEQUENCE: 8
cggaagagtg tctggagcaa                                               20

<210> SEQ ID NO 9
<211> LENGTH: 19
<212> TYPE: DNA
<213> ORGANISM: Artificial Sequence
<220> FEATURE:
<223> OTHER INFORMATION: Reverse Primer for hTERT

<400> SEQUENCE: 9
ggatgaagcg gagtctgga                                                19

<210> SEQ ID NO 10
<211> LENGTH: 20
<212> TYPE: DNA
<213> ORGANISM: Artificial Sequence
<220> FEATURE:
<223> OTHER INFORMATION: Forward Primer for TDGF

<400> SEQUENCE: 10
tccttctacg gacggaactg                                               20

<210> SEQ ID NO 11
<211> LENGTH: 20
<212> TYPE: DNA
<213> ORGANISM: Artificial Sequence

```
<220> FEATURE:
<223> OTHER INFORMATION: Reverse Primer for TDGF

<400> SEQUENCE: 11
agaaatgcct gaggaaagca                                          20

<210> SEQ ID NO 12
<211> LENGTH: 20
<212> TYPE: DNA
<213> ORGANISM: Artificial Sequence
<220> FEATURE:
<223> OTHER INFORMATION: Forward Primer for hNPY

<400> SEQUENCE: 12
tgctaggtaa caagcgactg                                          20

<210> SEQ ID NO 13
<211> LENGTH: 20
<212> TYPE: DNA
<213> ORGANISM: Artificial Sequence
<220> FEATURE:
<223> OTHER INFORMATION: Reverse Primer for hNPY

<400> SEQUENCE: 13
ctgcatgcat tggtaggatg                                          20

<210> SEQ ID NO 14
<211> LENGTH: 20
<212> TYPE: DNA
<213> ORGANISM: Artificial Sequence
<220> FEATURE:
<223> OTHER INFORMATION: Forward Primer for hNPY1R

<400> SEQUENCE: 14
accactgggt ctttggtgag                                          20

<210> SEQ ID NO 15
<211> LENGTH: 20
<212> TYPE: DNA
<213> ORGANISM: Artificial Sequence
<220> FEATURE:
<223> OTHER INFORMATION: Reverse Primer for hNPY1R

<400> SEQUENCE: 15
aaggcaaaga agaagccaca                                          20

<210> SEQ ID NO 16
<211> LENGTH: 23
<212> TYPE: DNA
<213> ORGANISM: Artificial Sequence
<220> FEATURE:
<223> OTHER INFORMATION: Forward Primer for hNPYR5

<400> SEQUENCE: 16
gggtccccac ttgctttgag ata                                      23

<210> SEQ ID NO 17
<211> LENGTH: 24
<212> TYPE: DNA
<213> ORGANISM: Artificial Sequence
<220> FEATURE:
<223> OTHER INFORMATION: Reverse Primer for hNPYR5

<400> SEQUENCE: 17
gttctttcct tggtaaacag tgag                                     24
```

```
<210> SEQ ID NO 18
<211> LENGTH: 20
<212> TYPE: DNA
<213> ORGANISM: Artificial Sequence
<220> FEATURE:
<223> OTHER INFORMATION: Forward Primer for mNPY

<400> SEQUENCE: 18
tggactgacc ctcgctctat                                                   20

<210> SEQ ID NO 19
<211> LENGTH: 20
<212> TYPE: DNA
<213> ORGANISM: Artificial Sequence
<220> FEATURE:
<223> OTHER INFORMATION: Reverse Primer for mNPY

<400> SEQUENCE: 19
tcaccacatg gaagggtctt                                                   20

<210> SEQ ID NO 20
<211> LENGTH: 20
<212> TYPE: DNA
<213> ORGANISM: Artificial Sequence
<220> FEATURE:
<223> OTHER INFORMATION: Forward Primer for mNPY1R

<400> SEQUENCE: 20
gtccttgcag tggcttcttc                                                   20

<210> SEQ ID NO 21
<211> LENGTH: 20
<212> TYPE: DNA
<213> ORGANISM: Artificial Sequence
<220> FEATURE:
<223> OTHER INFORMATION: Reverse Primer for mNPY1R

<400> SEQUENCE: 21
tgattcgctt ggtctcactg                                                   20

<210> SEQ ID NO 22
<211> LENGTH: 20
<212> TYPE: DNA
<213> ORGANISM: Artificial Sequence
<220> FEATURE:
<223> OTHER INFORMATION: Forward Primer for mNPY2R

<400> SEQUENCE: 22
gaggtgcagg tgatcctcat                                                   20

<210> SEQ ID NO 23
<211> LENGTH: 20
<212> TYPE: DNA
<213> ORGANISM: Artificial Sequence
<220> FEATURE:
<223> OTHER INFORMATION: Reverse Primer for mNPY2R

<400> SEQUENCE: 23
tttccactct cccatcaagg                                                   20

<210> SEQ ID NO 24
<211> LENGTH: 20
<212> TYPE: DNA
<213> ORGANISM: Artificial Sequence
<220> FEATURE:
<223> OTHER INFORMATION: Forward Primer for mNPYR5

<400> SEQUENCE: 24
```

```
tgtggattgt cccacaaaga                                               20

<210> SEQ ID NO 25
<211> LENGTH: 20
<212> TYPE: DNA
<213> ORGANISM: Artificial Sequence
<220> FEATURE:
<223> OTHER INFORMATION: Reverse Primer for mNPYR5

<400> SEQUENCE: 25
catccagcta acagcgaaca                                               20

<210> SEQ ID NO 26
<211> LENGTH: 20
<212> TYPE: DNA
<213> ORGANISM: Artificial Sequence
<220> FEATURE:
<223> OTHER INFORMATION: Forward Primer for Sox1

<400> SEQUENCE: 26
gggaaaacgg gcaaaataat                                               20

<210> SEQ ID NO 27
<211> LENGTH: 20
<212> TYPE: DNA
<213> ORGANISM: Artificial Sequence
<220> FEATURE:
<223> OTHER INFORMATION: Reverse Primer for Sox1

<400> SEQUENCE: 27
ccatctgggc ttcaagtgtt                                               20

<210> SEQ ID NO 28
<211> LENGTH: 20
<212> TYPE: DNA
<213> ORGANISM: Artificial Sequence
<220> FEATURE:
<223> OTHER INFORMATION: Forward Primer for Pax6

<400> SEQUENCE: 28
atgaggctca aatgcgactt                                               20

<210> SEQ ID NO 29
<211> LENGTH: 20
<212> TYPE: DNA
<213> ORGANISM: Artificial Sequence
<220> FEATURE:
<223> OTHER INFORMATION: Reverse Primer for Pax6

<400> SEQUENCE: 29
catttggccc ttcgattaga                                               20

<210> SEQ ID NO 30
<211> LENGTH: 21
<212> TYPE: DNA
<213> ORGANISM: Artificial Sequence
<220> FEATURE:
<223> OTHER INFORMATION: Forward Primer for MSI1

<400> SEQUENCE: 30
ttcgggtttg tcacgtttga g                                             21

<210> SEQ ID NO 31
<211> LENGTH: 20
<212> TYPE: DNA
<213> ORGANISM: Artificial Sequence
```

```
<220> FEATURE:
<223> OTHER INFORMATION: Reverse Primer for MSI1

<400> SEQUENCE: 31
ggcctgtata actccggctg                                               20

<210> SEQ ID NO 32
<211> LENGTH: 20
<212> TYPE: DNA
<213> ORGANISM: Artificial Sequence
<220> FEATURE:
<223> OTHER INFORMATION: Forward Primer for Nestin

<400> SEQUENCE: 32
aacagcgacg gaggtctcta                                               20

<210> SEQ ID NO 33
<211> LENGTH: 20
<212> TYPE: DNA
<213> ORGANISM: Artificial Sequence
<220> FEATURE:
<223> OTHER INFORMATION: Reverse Primer for Nestin

<400> SEQUENCE: 33
ttctcttgtc ccgcagactt                                               20

<210> SEQ ID NO 34
<211> LENGTH: 20
<212> TYPE: DNA
<213> ORGANISM: Artificial Sequence
<220> FEATURE:
<223> OTHER INFORMATION: Forward Primer for Sox3

<400> SEQUENCE: 34
gacgccttgt ttagctttgc                                               20

<210> SEQ ID NO 35
<211> LENGTH: 20
<212> TYPE: DNA
<213> ORGANISM: Artificial Sequence
<220> FEATURE:
<223> OTHER INFORMATION: Reverse Primer for Sox3

<400> SEQUENCE: 35
ttctcccatt cactccttgg                                               20

<210> SEQ ID NO 36
<211> LENGTH: 20
<212> TYPE: DNA
<213> ORGANISM: Artificial Sequence
<220> FEATURE:
<223> OTHER INFORMATION: Forward Primer for MAP2

<400> SEQUENCE: 36
gacatgcaag gcacagaaga                                               20

<210> SEQ ID NO 37
<211> LENGTH: 20
<212> TYPE: DNA
<213> ORGANISM: Artificial Sequence
<220> FEATURE:
<223> OTHER INFORMATION: Reverse Primer for MAP2

<400> SEQUENCE: 37
ttttccctca tgggagtcag                                               20
```

```
<210> SEQ ID NO 38
<211> LENGTH: 25
<212> TYPE: DNA
<213> ORGANISM: Artificial Sequence
<220> FEATURE:
<223> OTHER INFORMATION: Forward Primer for bi Oct4-3

<400> SEQUENCE: 38
atttgttttt tgggtagtta aaggt                                          25

<210> SEQ ID NO 39
<211> LENGTH: 27
<212> TYPE: DNA
<213> ORGANISM: Artificial Sequence
<220> FEATURE:
<223> OTHER INFORMATION: Reverse Primer for bi Oct4-3

<400> SEQUENCE: 39
ccaactatct tcatcttaat aacatcc                                        27

<210> SEQ ID NO 40
<211> LENGTH: 27
<212> TYPE: DNA
<213> ORGANISM: Artificial Sequence
<220> FEATURE:
<223> OTHER INFORMATION: Forward Primer for bi Oct4-4

<400> SEQUENCE: 40
ggatgttatt aagatgaaga tagttgg                                        27

<210> SEQ ID NO 41
<211> LENGTH: 25
<212> TYPE: DNA
<213> ORGANISM: Artificial Sequence
<220> FEATURE:
<223> OTHER INFORMATION: Reverse Primer for bi Oct4-4

<400> SEQUENCE: 41
cctaaactcc ccttcaaaat ctatt                                          25

<210> SEQ ID NO 42
<211> LENGTH: 25
<212> TYPE: DNA
<213> ORGANISM: Artificial Sequence
<220> FEATURE:
<223> OTHER INFORMATION: Forward Primer for bi Nanog

<400> SEQUENCE: 42
tggttaggtt ggttttaaat ttttg                                          25

<210> SEQ ID NO 43
<211> LENGTH: 26
<212> TYPE: DNA
<213> ORGANISM: Artificial Sequence
<220> FEATURE:
<223> OTHER INFORMATION: Reverse Primer for bi Nanog

<400> SEQUENCE: 43
aacccaccct tataaattct caatta                                         26
```